United States Patent [19]

Murayama et al.

[11] 3,941,744
[45] Mar. 2, 1976

[54] PIPERIDINE DERIVATIVES AND THEIR USE AS STABILIZERS

[75] Inventors: Keisuke Murayama; Syoji Morimura; Takao Yoshioka; Toshimasa Toda; Eiko Mori; Hideo Horiuchi; Susumu Higashida; Katsuaki Matsui; Tomoyuki Kurumada; Noriyuki Ohata; Hisayou Ohsawa, all of Tokyo, Japan

[73] Assignee: Sankyo Company Limited, Japan

[22] Filed: Mar. 12, 1973

[21] Appl. No.: 339,772

Related U.S. Application Data

[62] Division of Ser. No. 258,392, May 31, 1972, abandoned.

[30] Foreign Application Priority Data

June 5, 1971  Japan................................. 46-39630

[52] U.S. Cl. 260/45.8 N; 260/45.8 NZ; 260/293.87
[51] Int. Cl.$^2$............................................ C08K 5/00
[58] Field of Search ... 260/45.8 N, 45.8 NZ, 293.87

[56] References Cited
UNITED STATES PATENTS

| | | | |
|---|---|---|---|
| 2,684,965 | 7/1954 | Weston et al.................. | 260/293.87 |
| 3,126,393 | 3/1964 | Young............................ | 260/293.87 |
| 3,542,729 | 11/1970 | Murayama et al................ | 260/45.8 |

Primary Examiner—M. J. Welsh
Attorney, Agent, or Firm—Toren, McGeady and Stanger

[57] ABSTRACT

Piperidine derivatives having the formula

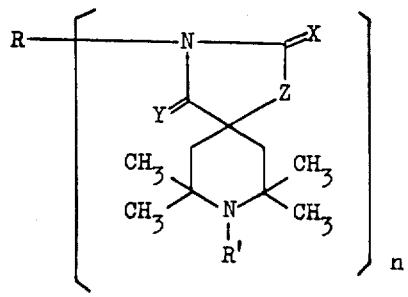

wherein

R' represents an alkyl group, a substituted alkyl group, an acyl group, an alkoxycarbonyl group, a substituted alkoxycarbonyl group, an amino group, a substituted amino group, or nitroso group;

X represents oxygen atom or sulfur atom;

Y represents oxygen atom, sulfur atom or a group of the formula $= N - R''$ in which $R''$ is hydrogen atom, an alkyl group or a substituted alkyl group;

Z represents oxygen atom or a group of the formula $>N - R'''$ in which $R'''$ is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group; an alkylenediphenylene group, a bis-(acyloxyalkylene) group, an alkylene-bis-(oxycarbonylalkyl) group, a dialkylene ether group or a diphenylene ether group, when n is 3, an alkanetriyl group, a tris(acyloxyalkylene) group, an alkane-tris(oxycarbonylakyl) group or a group of the group

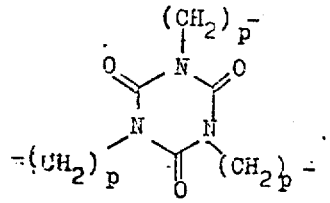

in which p is an integer of 1 through 8 inclusive, and, when n is 4, an alkanetetrayl group, a tetrakis-(acyloxyalkylene) group or an alkane-tetrakis-(oxycarbonylalkyl) group.

The piperidine derivatives (I) of this invention are prepared in various manners and useful as stabilizers for synthetic polymers against thermal- and photo-deterioration thereof.

24 Claims, No Drawings

PIPERIDINE DERIVATIVES AND THEIR USE AS STABILIZERS

This is a division of application Ser. No. 258,392 filed on May 31, 1972 and now abandoned.

This invention relates to new piperidine derivatives and their use as stabilizers.

More particularly, this invention is concerned with the piperidine derivatives having the formula

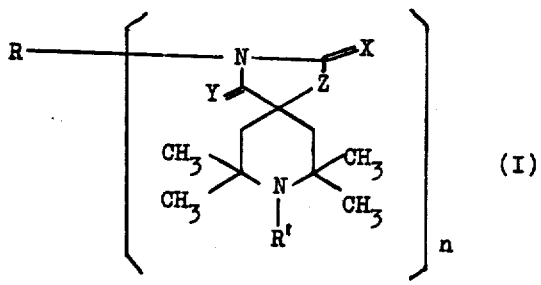

wherein
R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula = N - R'' in which R'' is hydrogen atom, an alkyl group or a substituted alkyl group;

Z represents oxygen atom or a group of the formula >N - R''' in which R''' is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group; when n is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group, when n is 3, an alkanetriyl group, a tris-(acyloxyalkylene) group, an alkane-tris-(oxycarbonylalkyl) group or a group of the group

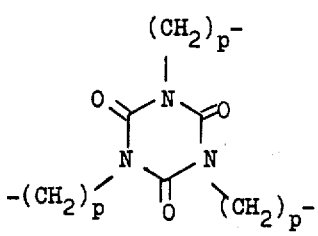

in which
p is an integer of 1 through 8 inclusive, and when n is 4, an alkane tetrayl group, a tetrakis-(acyloxyalkylene) group or an alkanetetrakis-(oxycarbonylalkyl) group.

The p's as appeared herein may be the same or different.

This invention is also concerned with stabilization of synthetic polymers against photo- and thermal-deterioration thereof by having incorporated therein, in a sufficient amount to prevent said deterioration, at least one of the piperidine derivatives (I).

The term "synthetic polymer" as used herein are intended to embrace polyolefins including
homopolymers of olefins such as low-density and high-density polyethylene, polypropylene, polystyrene, polybutadiene, polyisoprene and the like, and copolymers of olefins with other ethylenically unsaturated monomers such as ethylene-propylene copolymer, ethylene-butene copolymer, ethylene-vinyl acetate copolymer, styrene-butadiene copolymer, acrylonitrile-styrene-butadiene copolymer and the like;

polyvinyl chlorides and polyvinylidene chlorides including homopolymer of each of vinyl chloride and vinylidene chloride, vinyl chloride-vinylidene chloride copolymer and copolymers of each of vinyl chloride and vinylidene chloride with vinyl acetate or other ethylenically unsaturated monomers;

polyacetals such as polyoxymethylene and polyoxyethylene;

polyesters such as polyethylene terephthalate; polyamides such as 6-nylon, 6,6-nylon and 6,10-nylon; and polyurethanes.

In the above formula (I), R' may be exemplified by an alkyl group of 1 to 20 carbon atoms, e.g., methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl or eicosyl; a hydroxyalkyl group, e.g., 2-hydroxyethyl, allyl group, 2-propynyl group, a cyanoalkyl group, e.g., 2-cyanoethyl, an alkoxyalkyl group, e.g., 2-methoxyethyl or ethoxymethyl, an alkenyloxyalkyl group, e.g., vinyloxyethyl, an aryloxyalkyl group, e.g., phenoxyethyl, an alkylthioalkyl group, e.g., methylthioethyl, an epoxyalkyl group, e.g., 2,3-epoxypropyl, an acyloxyalkyl group, e.g., acetoxyethyl, octanoyloxyethyl, acryloyloxyethyl, benzoyloxyethyl, m-toluoyloxyethyl, m-methoxybenzoyloxyethyl or p-chlorobenzoyloxyethyl, an alkoxycarbonylalkyl group, e.g., ethoxycarbonylmethyl or phenoxycarbonylmethyl, an aralkyl group, e.g., benzyl, phenethyl, p-methylbenzyl or p-chlorobenzyl; an acyl group, e.g., acryloyl, an acryloyl group which is substituted with alkyl or phenyl, e.g., crotonoyl or cinnamoyl; an alkoxy carbonyl group, e.g., ethoxycarbonyl or acryloxycarbonyl; an aralkyloxycarbonyl group, e.g., benzyloxycarbonyl; amino group; an aroylamino group, e.g., benzoylamino or an alkylamino group, e.g., ethylamino; or nitroso group.

The group of the formula = N — R'' may be exemplified by imino, methylimino, acrylimino, 2-propynylimino, 2-hydroxyethylimino, 2-methoxyethylimino or bynzylimino.

The group of the formula >N - R''' may be exemplified by imino, methylimino, ethylimino, butylimino, acrylimino, 2-propynylimino, 2-hydroxyethylimino, ethoxymethylimino, 2-vinyloxyethylimino, 2-phenoxyethylimino, 2-acetoxyethylimino, 2-benzyloxyethylimino or benzylimino.

The substituent R may be exemplified, when n is 1, by the unsubstituted or substituted alkyl groups as illustrated above or 2,3-epoxypropylcarbonylmethyl; phenyl or naphthyl; a halogen- or alkyl-substituted phenyl or naphthyl group, e.g., p-tolyl, m-chlorophenyl or o-chlorophenyl; cyclohexyl; the unsubstituted or substituted alkoxycarbonyl groups as illustrated above; the group of the formula

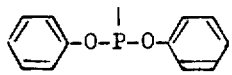

or the group of the formula

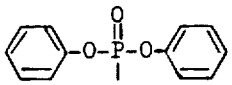

The substituent R, when n is 2, may be exemplified by a polymethylene group of 1 to 10 carbon atoms, e.g., trimethylene or hexamethylene; a group of the formula —(CH$_2$)$_p$—CH=CH—(CH$_2$)$_p$— in which p is an integer of 1 through 8 inclusive and p's may be the same or different herein, e.g., —CH$_2$—CH=CH—CH$_2$—; a phenylene group which may be substituted with alkyl, e.g.,

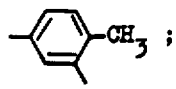

a group of the formula

a group of the formula

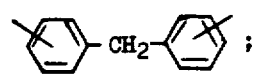

a group of the formula

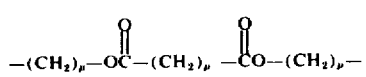

in which p is as defined above and p$_1$ is an integer of zero through 8 inclusive, e.g., —(CH$_2$)$_2$OCO(CH$_2$)$_4$COO(CH$_2$)—;
a group of the formula

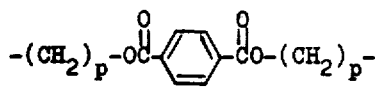

in which p is as defined above, e.g.,

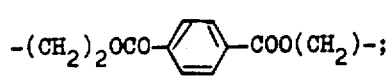

a group of the formula

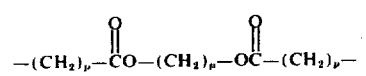

in which p is as defined above, e.g., —CH$_2$COO(CH$_2$)$_2$OCOCH$_2$—; a group of the formula —(CH$_2$)$_p$—O—(CH$_2$)$_p$— in which p is as defined above, e.g., —CH$_2$—O—CH$_2$—; or a group of the formula

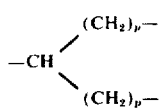

The substituent R, when n is 3, may be exemplified by a group of the formula -(CH$_2$)$_p$

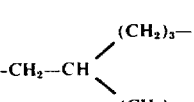

in which p is as defined above, e.g.,

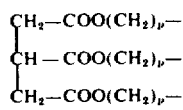

a group of the formula

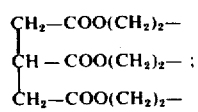

in which p is as defined above, e.g.,

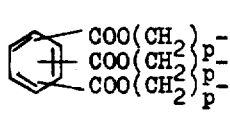

a group of the formula

in which p is as defined above, e.g.,

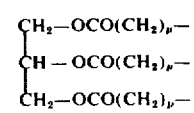

in which p is as defined above, e.g.,

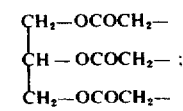

or a group of the formula

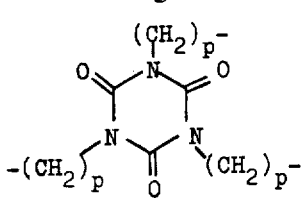

in which p is as defined above, e.g.,

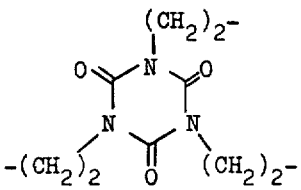

The substituent R, when n is 4, may be exemplified by a group of the formula

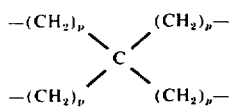

in which p is as defined above; a group of the formula

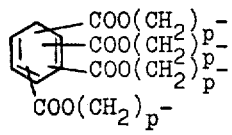

in which p is as defined above, e.g.,

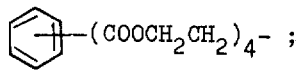

or a group of the formula

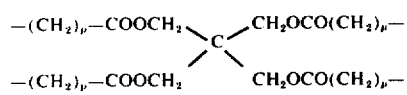

in which p is as defined above.

Synthetic polymers have been widely utilized in the art, in view of their excellent properties, in various forms or shapes, for example, filament, fibre, yarn, film, sheet, other molded article, latex and foram. However, these polymers have some drawbacks such as poor light- and heat-stabilities and the like. STated illustratively, polyolefins and polyurethane elastomers frequently tend to undergo severe deterioration when exposed to light such as sunlight or ultraviolet ray, and polyvinyl chloride and polyvinylidene chloride frequently tend to deteriorate and become colored by the action of light and heat together with elimination of hydrogen chloride therefrom. Polyamides are also frequently subjected to photo-deterioration. For the purpose of stabilizing these synthetic polymers against such deterioration, there have heretofore been proposed in the art a number of stabilizers; for example, for polyolefins, benzotriazole compounds and benzophenone compounds; for polyurethanes, phenol compounds and benzophenone compounds; and for polyvinyl chloride and polyvinylidine chloride, lead salts such as basic lead silicate and tribasic lead maleate, and organotin compounds such as dibutyltin laurate and dibutyltin maleate.

Although such prior stabilizers are known to be considerably satisfactory, there still remained some problems to be improved.

Thus, numerous attempts have been made in the art to find and develop new and more effective stabilizers.

As a result of our extensive studies, it has now been found that the new piperidine derivatives (I) of this invention can be satisfactorily prepared and exhibit a high stabilizing effect against photo- and thermal-deterioration of the synthetic polymers.

It is, accordingly, an object of this invention to provide new and useful piperidine derivatives (I).

Another object is to provide synthetic polymer composition stabilized against the deterioration thereof by having incorporated therein a sufficient amount to prevent the deterioration of at least one of the piperidine derivatives (I).

Other objects of this invention will become apparent to those skilled in the art from the following description.

In one aspect of this invention, the piperidine derivatives (I) are all new substances unknown in the art.

Among the piperidine derivatives (I) of this invention, particularly useful are the piperidine derivatives having the formula (I) wherein R' represents an alkyl group of 1 to 20 carbon atoms, a hydroxyalkyl group, allyl group, 2-propynyl group, a cyanoalkyl group, an alkoxyalkyl group, an alkenyloxyalkyl group, an aryloxyalkyl group, an alkylthioalkyl group, an epoxyalkyl group, an acyloxyalkyl group, an alkoxycarbonylalkyl group, an aralkyl group, acryloyl group, an acryloyl group which is substituted with alkyl or phenyl, an aralkyloxycarbonyl group, amino group or an amino group which is substituted with aroyl or alkyl;

R represents, when n is 1, the above-defined unsubstituted or substituted alkyl group, a phenyl or naphthyl group which may be substituted with halogen or alkyl in the aryl moiety, a cycloalkyl group, an alkoxycarbonyl group, an aralkyloxycarbonyl group, the group of the formula

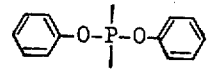

or the group of the formula

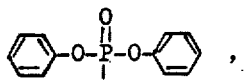

when n is 2, a polymethylene group of 1 to 10 carbon atoms, a group of the formula —(CH$_2$)$_p$—CH=CH-(CH$_2$)$_p$— in which p is an integer of 1 through 8 inclusive and p's may be the same or different, a phenylene group which may be substituted with alkyl, a group of the formula,

a group of the formula

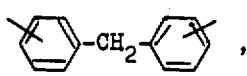

a group of the formula

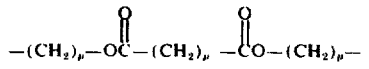

in which $p$ and $p_1$ are as defined above, a group of the formula

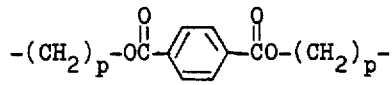

in which $p$ is as defined above, a group of the formula

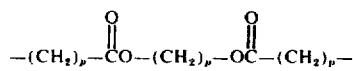

in which $p$ is as defined above, a group of the formula $-(CH_2)_p-O-(CH_2)_p-$ in which $p$ is as defined above or a group of the formula

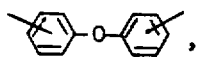

when $n$ is 3, a group of the formula

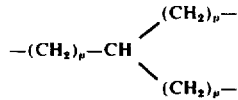

in which $p$ is as defined above, a group of the formula

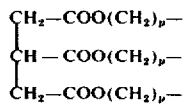

in which p is as defined above, a group of the formula

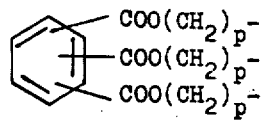

in which $p$ is as defined above, a group of the formula

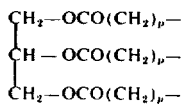

in which p is as defined above or a group of the formula

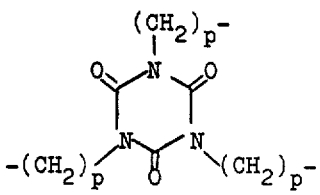

in which $p$ is as defined above, and, when $n$ is 4, a group of the formula

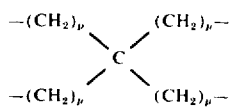

in which $p$ is as defined above, a group of the formula

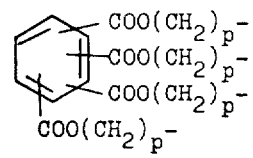

in which $p$ is as defined above or a group of the formula

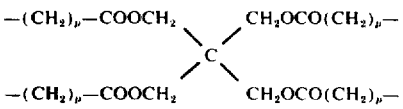

in which $p$ is as defined above, Y represents oxygen atom, sulfur atom or a group of the formula $=N-R''$ in which $R''$ is hydrogen atom or the above-defined unsubstituted or substituted alkyl group; Z represents oxygen atom or a a group of the formula $>N-R'''$ in which $R'''$ is hydrogen atom or the above-defined unsubstituted or substituted alkyl group.

More preferable group of the piperidine derivatives (I) of this invention can be represented by the following formula (II):

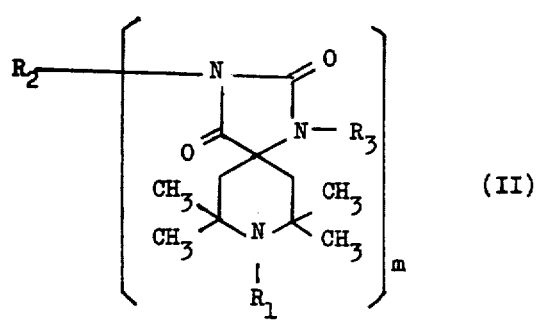

(II)

In the above formula (II), $R_1$ represents an alkyl group, allyl group, an aralkyl group an acyloxyalkyl group or a hydroxyalkyl group or 2,3-epoxypropyl group;

$R_3$ represents hydrogen atom or an alkyl group; m is an integer of 1 or 2; and $R_2$ represents when m is 1, an alkyl group, allyl group, an aralkyl group, an acyloxyalkyl group or 2,3-epoxypropyl group, and when m is 2, an alkylene group, a group of the formula

or a group of the formula —$(CH_2)_p$—O—$(CH_2)_p$— in which p is as defined above.

Representatives of the new piperidine derivatives (I) of this invention are illustratively listed below. However, it should be understood that these illustrated compounds are not contemplated to be limiting the scope of this invention.

1. 1,3,8-triaza-3,7,7,8,9,9-hexamethyl-spiro[4.5]-decane-2,4-dione
2. 1,3,8-triaza-3-butyl-7,7,8,9,9-pentamethyl-spiro[4.5]decane-2,4-dione
3. 1,3,8-triaza-7,7,8,9,9-pentamethyl-3-octyl-spiro[4.5]decane-2,4-dione
4. 1,3,8-triaza-3,8-diethyl-7,7,9,9-tetramethyl-spiro[4.5]decane-2,4-dione
5. 1,3,8-triaza-3-butyl-8-ethyl-7,7,9,9-tetramethyl-spiro[4.5]decane-2,4-dione
6. 1,3,8-triaza-8-ethyl-7,7,9,9-tetramethyl-3-octyl-spiro[4.5]decane-2,4-dione
7. 1,3,8-triaza-1,3,7,7,8,9,9-heptamethyl-spiro[4.5]-decane-2,4-dione
8. 1,3,8-triaza-3-butyl-1,8-diethyl-7,7,9,9-tetramethyl-spiro[4.5]decane-2,4-dione
9. 1,3,8-triaza-1-butyl-8-ethyl-7,7,9,9-tetramethyl-3-octyl-spiro[4.5]decane-2,4-dione
10. 3,8-diaza-7,7,8,9,9-pentamethyl-3-octadecyl-1-oxa-spiro[4.5]decane-2,4-dione
11. 8-allyl-1,3,8-triaza-7,7,9,9-tetramethyl-3-octyl-spiro[4.5]decane-2,4-dione
12. 1,3,8-triaza-8-benzyl-7,7,9,9-tetramethyl-3-octyl-spiro[4.5]decane-2,4-dione
13. 1,3,8-triaza-8-benzyl-7,7,9,9-tetramethyl-3-octadecyl-spiro[4.5]decane-2,4-dione
14. 1,3,8-triaza-3,7,7,8,9,9-hexamethyl-1-ethoxymethyl-spiro[4.5]decane-2,4-dione
15. 1,3,8-triaza-3,7,7,8,9,9-hexamethyl-1-(2-phenoxyethyl)-spiro[4.5]decane-2,4-dione
16. 1,3,8-triaza-3,7,7,8,9,9-hexamethyl-1-(2-vinyloxyethyl)-spiro[4.5]decane-2,4-dione
17. 1,3,8-triaza-3-butyl-8-(2-hydroxyethyl)-7,7,9,9-tetramethyl-spiro[4.5]decane-2,4-dione
18. 1,3,8-triaza-8-(2-hydroxyethyl)-7,7,9,9-tetramethyl-3-octyl-spiro[4.5]decane-2,4-dione
19. 1,3,8-triaza-8-(2-cyanoethyl)-1,3,7,7,9,9-hexamethyl-spiro[4.5]decane-2,4-dione
20. 1,3,8-triaza-3-butyl-8-(2,3-epoxypropyl)-7,7,9,9-tetramethyl-spiro[4.5]decane-2,4-dione
21. 1,3,8-triaza-8-(2-ethoxyethyl)-3,7,7,9,9-pentamethyl-spiro[4.5]decane-2,4-dione
22. 1,3,8-triaza-8-crotonoyl-3,7,7,9,9-pentamethyl-spiro[4.5]decane-2,4-dione
23. 1,3,8-triaza-8-cinnamoyl-3,7,7,9,9-pentamethyl-spiro[4.5]decane-2,4-dione
24. 1,3,8-triaza-8-benzyloxycarbonyl-3-butyl-7,7,9,9-tetramethyl-spiro[4.5]decane-2,4-dione
25. 1,3,8-triaza-3,7,7,9,9-pentamethyl-8-nitroso-spiro[4.5]decane-2,4-dione
26. 1,3,8-triaza-3-butyl-7,7,9,9-tetramethyl-8-nitroso-spiro[4.5]decane-2,4-dione
27. 8-amino-1,3,8-triaza-3-butyl-7,7,9,9-tetramethyl-spiro[4.5]decane-2,4-dione
28. 1,3,8-triaza-8-benzamido-3-butyl-7,7,9,9-tetramethyl-spiro[4.5]decane-2,4-dione
29. 1,3,8-triaza-3-butyl-8-ethylamino-7,7,9,9-tetramethyl-spiro[4.5]decane-2,4-dione
30. 3-allyl-1,3,8-triaza-7,7,8,9,9-pentamethyl-spiro[4.5]-decane-2,4-dione
31. 3-allyl-1,3,8-triaza-8-ethyl-7,7,9,9-tetramethyl-spiro[4.5]decane-2,4-dione
32. 1,3-diallyl-1,3,8-triaza-7,7,8,9,9-pentamethyl-spiro[4.5]decane-2,4-dithione
33. 3,8-diallyl-1,3,8-triaza-7,7,9,9-tetramethyl-spiro[4.5]decane-2,4-dione
34. 3,8-diallyl-1,3,8-triaza-1-benzyl-7,7,9,9-tetramethylspiro[4.5]decane-2,4-dione
35. 3-allyl-1,3,8-triaza-8-(2,3-epoxypropyl)-7,7,9,9-tetra-methylspiro[4.5]decane-2,4-dione p
36. 3-allyl-1,3,8-triaza-8-benzyl-7,7,9,9-tetramethyl-spiro[4.5]decane-2,4-dione
37. 1,3,8-triaza-7,7,9,9-tetramethyl-3,8-di(2-propynyl)spiro[4.5]decane-2,4-dione
38. 1,3,8-triaza-8-(2,3-epoxypropyl)-7,7,9,9-tetramethyl-3-(2-propynyl)-spiro[4.5]decane-2,4-dione
39. 1,3,8-triaza-3,8-bis(2-hydroxyethyl)-7,7,9,9-tetramethylspiro[4.5]decane-2,4-dione
40. 1,3,8-triaza-8-cyanomethyl-3-(3-hydroxypropyl)-7,7,9,9-tetramethyl-spiro[4.5]decane-2,4-dione
41. 1,3,8-triaza-7,7,9,9-tetramethyl-3,8-bis(2-methoxyethyl)spiro[4.5]decane-2,4-dione
42. 1,3,8-triaza-1,7,7,9,9-pentamethyl-3,8-bis(2-methoxyethyl)spiro[4.5]decane-2,4-dione
43. 1,3,8-triaza-3-ethoxymethyl-7,7,8,9,9-pentamethyl-spiro[4.5]decane-2,4-dione
44. 1,3,8-triaza-8-ethyl-7,7,9,9-tetramethyl-3-(2-vinyloxyethyl)-spiro[4.5]decane-2,4-dione
45. 8-allyl-1,3,8-triaza-7,7,9,9-tetramethyl-3-(2-phenoxyethyl)-spiro[4.5]decane-2,4-dione
46. 3-(2-acetoxyethyl)-1,3,8-triaza-8-benzyl-7,7,9,9-tetramethyl-spiro[4.5]decane-2,4-dione
47. 3,8-bis(2-acetoxyethyl)-1,3,8-triaza-7,7,9,9-tetramethylspiro[4.5]decane-2,4-dione
48. 1,3,8-triaza-2,2,6,6-tetramethyl-3,8-bis(2-octanoyloxyethyl)-spiro[4.5]decane-2,4-dione
49. 8-acryloyl-3-(2-acryloyloxyethyl)-1,3,8-triaza-7,7,9,9-tetramethyl-spiro[4.5]decane-2,4-dione
50. 3,8-bis(2-acryloyloxyethyl)-1,3,8-triaza-7,7,9,9-tetramethyl-spiro[4.5]decane-2,4-dione
51. 1,3,8-triaza-3-(2-benzoyloxyethyl)-8-ethyl-7,7,9,9-tetramethyl-spiro[4.5]decane-2,4-dione
52. 1,3,8-triaza-3,8-bis(2-benzoyloxyethyl)-7,7,9,9-tetramethyl-spiro[4.5]decane-2,4-dione 53. 1,3,8-triaza-7,7,9,9-tetramethyl-3,8-bis(2-m-toluoyloxyethyl)-spiro[4.5]decane-2,4-dione
54. 3,8-bis(2-o-anisoyloxyethyl)-1,3,8-triaza-7,7,9,9-tetramethyl-spiro[4.5]decane-2,4-dione
55. 1,3,8-triaza-3,8-bis(2-p-chlorobenzoyloxyethyl)-7,7,9,9-tetramethyl-spiro[4.5]decane-2,4-dione
56. 1,3,8-triaza-3,8-bis(2--cyanoethyl)-7,7,9,9-tetramethylspiro[4.5]decane-2,4-dione
57. 1,3,8-triaza-7,7,8,9,9-pentamethyl-3-(2-methylthioethyl)sprio[4.5]decane-2,4-dione
58. 1,3,8-triaza-3-(2,3-epoxypropyl)-7,7,8,9,9-pentamethylspiro[4.5]decane-2,4-dione
59. 1,3,8-triaza-3,8-bis(2,3-epoxypropyl)-7,7,9,9-tetramethylspiro[4.5]decane-2,4-dione
60. 1,3,8-triaza-3-ethoxycarbonylmethyl-7,7,8,9,9-pentamethylspiro[4.5]decane-2,4-dione
61. 1,3,8-triaza-3-(2,3-epoxypropyloxycarbonylmethyl)7,7,8,9,9-pentamethyl-spiro[4.5]decane-2,4-dione
62. 1,3,8-triaza-7,7,8,9,9-pentamethyl-3-phenoxycarbonylmethyl-spiro[4.5]decane-2,4-dione
63. 1,3,8-triaza-3-ethoxycarbonyl-7,7,8,9,9-pentamethylspiro[4.5]decane-2,4-dione
64. 1,3,8-triaza-3-benzyl-7,7,8,9,9-pentamethyl-spiro[4.5]decane-2,4-dione
65. 1,3,8-triaza-3-benzyl-7,7,9,9-tetramethyl-8-octyl-spiro[4.5]decane-2,4-dione
66. 1,3,8-triaza-3-benzyl-1,8-diethyl-7,7,9,9-tetramethylspiro[4.5]decane-2,4-dione
67. 1,3,8-triaza-1,3-dibenzyl-7,7,8,9,9-pentamethyl-spiro[4.5]decane-2,4-dithione
68. 1,3,8-triaza-7,7,9,9-tetramethyl-3-phenethyl-8-(2-propynyl)spiro[4.5]decane-2,4-dione
69. 1,3,8-triaza-3,8-dibenzyl-7,7,9,9-tetramethyl-spiro[4.5]decane-2,4-dione
70. 1,3,8-triaza-3,8-dibenzyl-1,7,7,9,9-pentamethyl-spiro[4.5]decane-2,4-dione
71. 1,3,8-triaza-3,8-dibenzyl-1-butyl-7,7,9,9-tetramethylspiro[4.5]decane-2,4-dione
72. 1,3,8-triaza-3,8-dibenzyl-1-(2-hydroxyethyl)-7,7,9,9-tetramethyl-spiro[4.5]decane-2,4-dione
73. 1-(2-acetoxyethyl)-1,3,8-triaza-3,8-dibenzyl-7,7,9,9-tetramethyl-spiro[4.5]decane-2,4-dione
74. 1,3,8-triaza-1-(2-benzoyloxyethyl)-3,8-dibenzyl-7,7,9,9-tetramethyl-spiro[4.5]decane-2,4-dione
75. 1,3,8-triaza-3,8-dibenzyl-7,7,9,9-tetramethyl-1-(2-propynyl)-spiro[4.5]decane-2,4-dione
76. 1,3,8-triaza-1,3,8-tribenzyl-7,7,9,9-tetramethyl-spiro[4.5]decane-2,4-dione
77. 1,3,8-triaza-3-benzyl-8-(2,3-epoxypropyl)-7,7,9,9-tetramethyl-spiro[4.5]decane-2,4-dione
78. 1,3,8-triaza-7,7,8,9,9-pentamethyl-3-(p-methylbenzyl)spiro[4.5]decane-2,4-dione
79. 1,3,8-triaza-3-(p-chlorobenzyl)-7,7,8,9,9-pentamethylspiro[4.5]decane-2,4-dione
80. 8-acryloyl-1,3,8-triaza-3-benzyl-7,7,9,9-tetramethylspiro[4.5]decane-2,4-dione
81. 1,3,8-triaza-3-cyclohexyl-7,7,8,9,9-pentamethyl-spiro[4.5]decane-2,4-dione
82. 1,3,8-triaza-3-cyclohexyl-8-(2,3-epoxypropyl)-7,7,9,9-tetramethyl-spiro[4.5]decane-2,4-dione
83. 1,3,8-triaza-8-benzyl-3-cyclohexyl-7,7,9,9-tetramethyl-spiro[4.5]decane-2,4-dione
84. 1,3,8-triaza-8-benzyl-4-benzylimino-3-cyclohexyl-7,7,9,9-tetramethyl-spiro[4.5]decane-2-one
85. 1,3,8-triaza-7,7,8,9,9-pentamethyl-3-phenylspiro[4.5]decane-2,4-dione
86. 1,3,8-triaza-8-(2,3-epoxypropyl)-7,7,9,9-tetramethyl-3-phenyl-spiro[4.5]decane-2,4-dione
87. 1,3,8-triaza-4-amino-7,7,8,9,9-pentamethyl-3-phenylspiro[4.5]decane-2-one
88. 1,3,8-triaza-7,7,8,9,9-pentamethyl-4-methylimino-3-phenyl-spiro[4.5]decane-2-one
89. 1,3,8-triaza-4-imino-7,7,8,9,9-pentamethyl-3-phenyl-spiro[4.5]decane-2-thione
90. 8-allyl-4-allylimino-1,3,8-triaza-7,7,9,9-tetramethy-3-phenyl-spiro[4.5]decane-2-one
91. 1,3,8-triaza-8-(2-hydroxyethyl)-4-(2-hydroxyethylimino)-7,7,9,9-tetramethyl-3-phenyl-spiro[4.5]decane-2-one
92. 1,3,8-triaza-1,7,7,9,9-pentamethyl-8-(2-methoxyethyl)-4-(2-methoxyethylimino)-3-phenyl-spiro[4.5]decane-2-one
93. 1,3,8-triaza-1,8-dibenzyl-7,7,9,9-tetramethyl-3-phenyl-spiro[4.5]decane-4-one-2-thione
94. 3,8-diaza-4-amino-7,7,8,9,9-pentamethyl-3-(α-naphthyl)-1-oxa-spiro[4.5]decane-2-thione
95. 1,3,8-triaza-8-benzyl-7,7,9,9-tetramethyl-3-(p-tolyl)spiro[4.5]decane-2,4-dione
96. 3,8-diaza-7,7,8,9,9-pentamethyl-1-oxa-3-(p-tolyl)spiro[4.5]decane-2,4-dione
97. 3,8-diaza-4-imino-7,7,8,9,9-pentamethyl-1-oxa-3-(p-tolyl)spiro[4.5]decane-2-one
98. 3,8-diaza-3-(o-chlorophenyl)-7,7,8,9,9-pentamethyl-1-oxa-spiro[4.5]decane-2,4-dione
99. 3,8-diaza-3-(o-chlorophenyl)-7,7,8,9.9-pentamethyl-4-methylimino-1-oxa-spiro[4.5]decane-2-one
100. 1,3,8-triaza-7,7,8,9,9-pentamethyl-3-diphenoxyphosphinospiro[4.5]decane-2,4-dithione
101. 1,3,8-triaza-7,7,8,9.9-pentamethyl-3-diphenoxyphosphinylspiro[4.5]decane-2,4-dithione
102. 1,3-bis(1,3,8-triaza-1,7,7,8,9,8-hexamethyl-2,4-dioxospiro[4.5]-3-decyl)propane
103. 1,6-bis(1,3,8-triaza-7,7,8,9,9-pentamethyl-2,4-dioxospiro[4.5]-3-decyl)hexane
104. 1,6-bis(1,3,8-triaza-1,7,7,8,9,9-hexamethyl-2,4-dioxospiro[4.5]-3-decyl)hexane
105. 1,6-bis[1,3,8-triaza-7,7,9,9-tetramethyl-2,4-dioxo-8-(2-propynyl)-spiro[4.5]-3-decyl]hexane
106. 1,6-bis[1,3,8-triaza-8-(2,3-epoxypropyl)-7,7,9,9-tetramethyl-2,4-dioxo-spiro[4.5]-3-decyl]-hexane
107. 1,6-bis(1,3,8-triaza-8-benzyl-7,7,9,9-tetramethyl-2,4-dioxo-spiro[4.5]-3-decyl)hexane
108. 1,4-bis(1,3,8-triaza-1,7,7,8,9,9-hexamethyl-2,4-dioxospiro[4.5]-3-decyl)trans-2-butene
109. 2,2'-bis(1,3,8-triaza-7,7,8,9,9-pentamethyl-2,4-dioxospiro[4.5]-3-decyl)diethylether
110. 2,2'-bis(1,3,8-triaza-1,7,7,8,9,9-hexamethyl-2,4-dioxospiro[4.5]-3-decyl)diethylether
111. α,α'-bis(1,3,8-triaza-7,7,8,9,9-pentamethyl-2,4-dioxospiro[4.5]-3-decyl)-p-xylene
112. αα'-bis(1,3,8-triaza-1,7,7,8,9,9-hexamethyl-2,4-dioxospiro[4.5]-3-decyl)-p-xylene
113. α,α'-bis[1,3,8-triaza-8-(2,3-epoxypropyl)-7,7,9,9-tetramethyl-2,4-dioxo-spiro[4.5]-3-decyl]-p-xylene
114. α,α'-bis(1,3,8-triaza-8-benzyl-7,7,9,9-tetramethyl-2,4-dioxo-spiro[4.5]-3-decyl)-p-xylene
115. 2,4-bis(1,3,8-triaza-7,7,8,9,9-pentamethyl-2,4-dioxospiro[4.5]-3-decyl)toluene
116. 2,4-bis(3,8-diaza-4-imino-7,7,8,9,9-pentamethyl-1-oxa-2-oxo-spiro[4.5]-3-decyl)toluene 117. 4,4'-bis(1,3,8-triaza-7,7,8,9,9-pentamethyl-2,4-dioxospiro[4.5]-3-decyl)diphenylmethane
118. 4,4'-bis[1,3,8-triaza-8-(2,3-epoxypropyl)-7,7,9,9-tetramethyl-2,4-dioxo-sprio[4.5]-3-decyl]-diphenylmethane
119. 4,4'-bis[1,3,8-triaza-7,7,9,9-tetramethyl-2-oxo-8-(2-propynyl)-4-(2-propynylimino)-spiro[4.5]-3-decyl]-diphenylmethane p
120. 4,4'-bis(1,3,8-triaza-7,7,8,9,9-pentamethyl-2,4-dioxospiro[4.5]-3-decyl)diphenylether
121. bis[2-(1,3,8-triaza-7,7,8,9,9-pentamethyl-2,4-dioxospiro[4.5]-3-decyl)ethyl]adipate
122. bis [2-(1,3,8-triaza-7,7,8,9,9-pentamethyl-2,4-dioxospiro[4.5]-3-decyl)ethyl]terephthalate
123. ethyleneglycol bis(1,3,8-triaza-7,7,8,9,9-pentamethyl-2,4-dioxo-spiro[4.5]-3-decylmethylcarboxylate)
124. 4-(1,3,8-triaza-7,7,8,9,9-pentamethyl-2,4-dioxo-spiro[4.5]-3-decylmethyl)-1,7-bis(1,3,8-triaza-7,7,8,9,9-pentamethyl-2,4-dioxo-spiro[4.5]-3-decyl)heptane
125. tris[2-(1,3,8-triaza-7,7,8,9,9-pentamethyl-2,4-dioxospiro[4.5]-3-decyl)ethyl]tricarballylate
126. tris[2-(1,3,8-triaza-7,7,8,9,9-pentamethyl-2,4-dioxospiro[4.5]-3-decyl)ethyl]trimellitate
127. tris(1,3,8-triaza-7,7,8,9,9-pentamethyl-2,4-dioxospiro[4.5]-3-decyl)acetin
128. 2,2',2''-tris[1,3,8-triaza-8-(2,3-epoxypropyl)-7,7,9,9-tetramethyl-2,4-dioxo-spiro[4.5]-3-decyl]-triethyl-isocyanurate
129. tetrakis [2-(1,3,8-triaza-7,7,8,9,9-pentamethyl-2,4-dioxo-spiro[4.5]-3-decyl)ethyl]pyromellitate
130. pentaerythritol tetrakis(1,3,8-triaza-7,7,8,9,9-pentamethyl-2,4-dioxo-spiro[4.5]-3-decylmethylcarboxylate)

In view of stabilizing effects, the following piperidine derivatives (I) are, in particular, preferable and effective:

1,3,8-triaza-3-butyl-7,7,8,9,9-pentamethyl-spiro[4.5]decane-2,4-dione,
1,3,8-triaza-7,7,8,9,9-pentamethyl-3-octyl-spiro[4.5]decane-2,4-dione,
8-allyl-1,3,8-triaza-7,7,9,9-tetramethyl-3-octyl-spiro[4.5]decane-2,4-dione,
1,3,8-triaza-8-benzyl-7,7,9,9-tetramethyl-3-octyl-spiro[4.5]-decane-2,4-dione,
1,3,8-triaza-8-(2-hydroxyethyl)-7,7,9,9--tetramethyl-3-octylspiro[4.5]-decane-2,4-dione,
1,3,8-triaza-3-butyl-8-(2,3-epoxypropyl)-7,7,9,9-tetramethylspiro[4.5]-decane-2,4-dione,
3-allyl-1,3,8-triaza-7,7,8,9,9-pentamethyl-spiro[4.5]decane-2,4-dione,
3,8-diallyl-1,3,8-triaza-7,7,9,9-tetramethyl-spiro[4.5]decane-2,4-dione,
3-allyl-1,3,8-triaza-(2,3-epoxypropyl)-7,7,9,9-tetramethylspiro[4.5]decane-2,4-dione,
3,8-bis(2-acetoxyethyl)-1,3,8-triaza-7,7,9,9-tetramethylspiro[4.5]decane-2,4-dione,
1,3,8-triaza-3-(2,3-epoxypropyl)-7,7,8,9,9-pentamethylspiro[4.5]decane-2,4-dione
1,3,8-triaza-3,8-di(2,3-epoxypropyl)7,7,9,9-tetramethylspiro[4.5]decane-2,4-dione,
1,3,8-triaza-3,8-dibenzyl-1,7,7,9,9-pentamethylspiro[4.5]decane-2,4-dione,
1,3-bis(1,3,8-triaza-1,7,7,8,9,9-hexamethyl-2,4-dioxo-spiro[4.5]-3-decyl)propane,
1,6-bis(1,3,8-triaza-1,7,7,8,9,9-hexamethyl-2,4-dioxospiro[4.5]-3-decyl)hexane,
2,2'-bis(1,3,8-triaza-7,7,8,9,9-pentamethyl-2,4-dioxospiro[4.5]-3-decyl)diethylether,
2,2'-bis(1,3,8-triaza-1,7,7,8,9,9-hexamethyl-2,4-dioxospiro[4.5]-3-decyl)diethylether,
1,3,8-triaza-1,3,7,7,8,9,9-heptamethyl-spiro[4.5]-decane-2,4-dione and
α,α'-bis(1,3,8-triaza-1,7,7,8,9,9-hexamethyl-2,4-dioxospiro[4.5]-3-decyl)-p-xylene.

The piperidine derivatives (I) of this invention may be readily prepared in various manners. For instance, they are prepared by any of the thirteen routes as illustratively shown below.

1. The compound (III) or the alkalimetal salt thereof is reacted with the halide ($R_0 - X_1$) in a molar ratio of 1 : 2 by heating in the presence or absence of a base to produce the compound (IV).

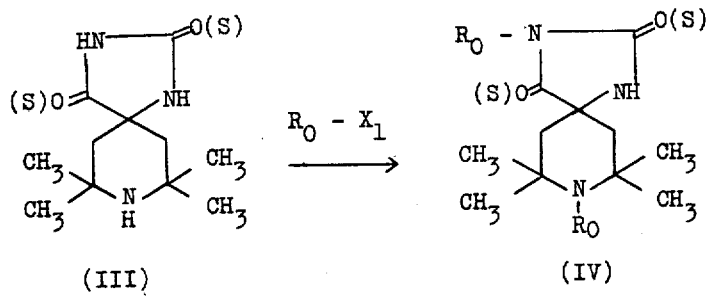

(III)   (IV)

In the above formulae, R represents an alkyl group, allyl group, 2-propynyl group, an epoxyalkyl group or an aralkyl group and $X_1$ represents a halogen atom.

This method will be more fully exemplified by Examples 1 and 2. and provide, for example, those compounds designated by Nos. 1, 4, 33, 37, 59 and 69 hereinabove.

2. The compound (V) is reacted with the halide ($R_4—X_1$) by heating in the presence or absence of a base to produce the compound (VI).

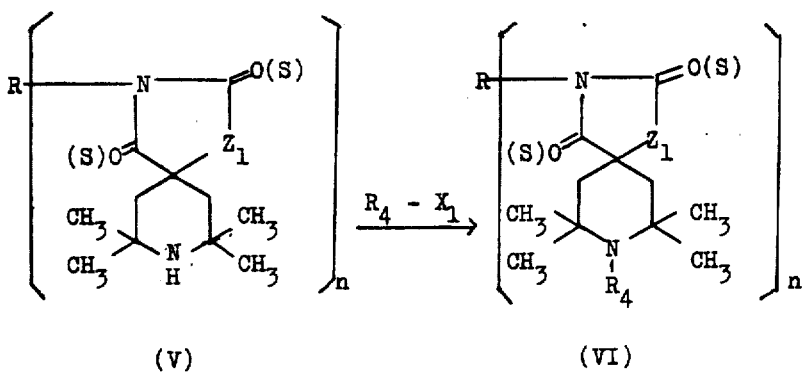

(V)         (VI)

In the above formulae, R and n are as defined above, $R_4$ represents an alkyl group, allyl group, 2-propynyl group, a cyanoalkyl group, an epoxyalkyl group, an aralkyl group, an acyl group or nitroso group, $Z_1$ represents oxygen atom or the group —NH— and $X_1$ represents a halogen atom.

This method will be more fully exemplified by Examples 3, 4 and 5 and provide, for example, those compounds designated by Nos. 2, 3, 5, 6, 10, 11, 12, 13, 20, 25, 26, 30, 31, 35, 36, 38, 40, 43, 44, 45, 46, 49, 51, 57, 58, 60, 64, 68, 77, 78, 79, 80, 81, 82, 83, 85, 86, 95, 96, 98, 103, 105, 106, 107, 109, 111, 113, 114, 115, 117, 118, 120, 121, 122, 123, 124 and 128 hereinabove.

3. The compound (VII) is reacted with the halide ($R_5$—$X_1$) by heating in the presence of a base to produce the compound (VIII).

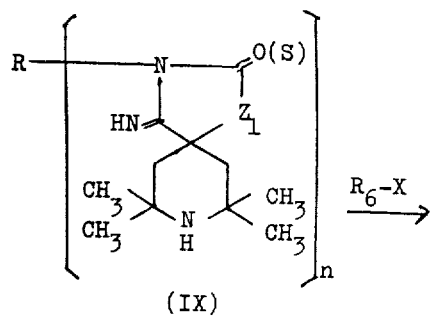

(IX)

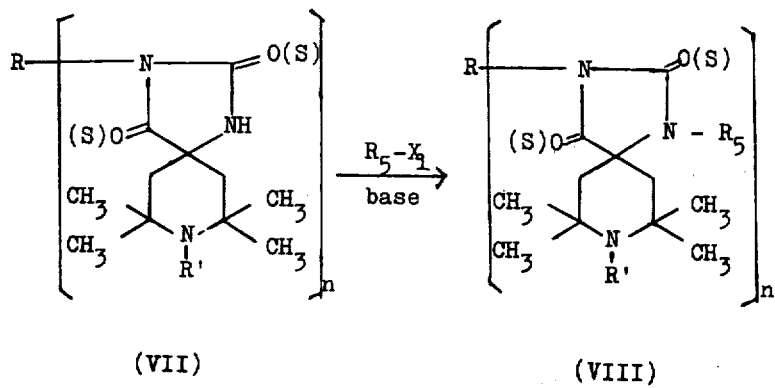

(VII)         (VIII)

In the above formulae, R, R' and n are as defined above, $R^5$ represents an alkyl group, allyl group, 2-propynyl group, a hydroxyalkyl group, an alkoxyalkyl group, an alkenyloxyalkyl group, an aryloxyalkyl group, an acyloxyalkyl group or an aralkyl group and $X_1$ represents a halogen atom.

This method will be more fully exemplified by Example 6 and provide, for example, those compounds designated by Nos. 7, 8, 9, 14, 15, 16, 19, 32, 34, 42, 66, 67, 70, 71, 72, 73, 74, 75, 76, 92 and 93 hereinabove.

4. The compound (IX) is reacted with the halide ($R_6$-X) by heating in the presence or absence of a base to produce the compound (X)

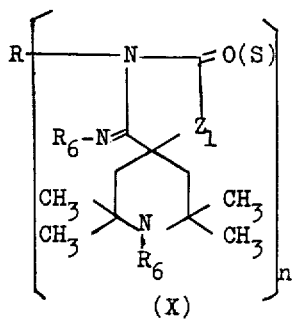

(X)

In the above formulae, R, n, X and $Z_1$ are as defined above and $R_6$ represents an alkyl group, allyl group, 2-propynyl group, a hydroxyalkyl group, an alkoxyalkyl group or an aralkyl group.

This method will be more fully exemplified by Example 7 and provide, for example, those compounds designated by Nos. 84, 88, 90, 91, 92, 99 and 119 hereinabove. (5) The compound (XI) is reacted with formaldehyde and formic acid to produce the compound (XII).

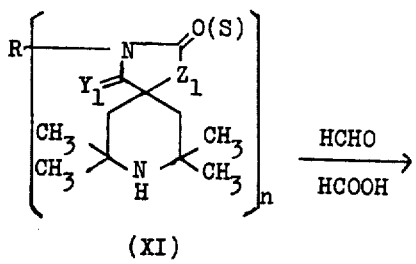

(XI)

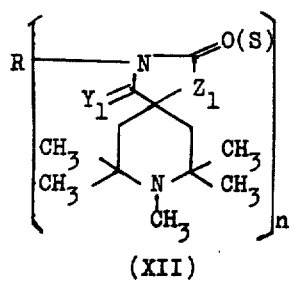

(XII)

In the above formulae, R, n and $Z_1$ are as defined above and $Y_1$ represents oxygen atom, sulfur atom or the group = NH.

This method will be more fully exemplified by Example 8 and provide, for example, those compounds designated by Nos. 2, 3, 10, 30, 64, 81, 85, 87, 89, 94, 97, 103, 109, 111, 115, 116 and 117 hereinabove.

6. The compound (XIII) is reacted with ethylene oxide by heating under pressure in the presence of an acid to produce the compound (XIV).

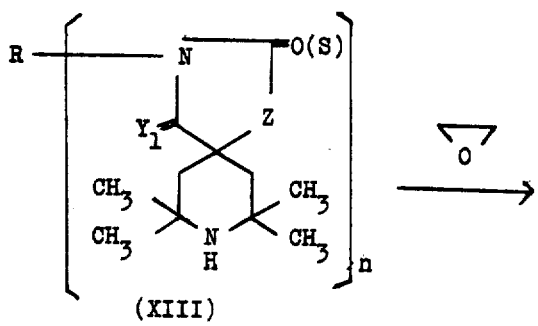

(XIII)

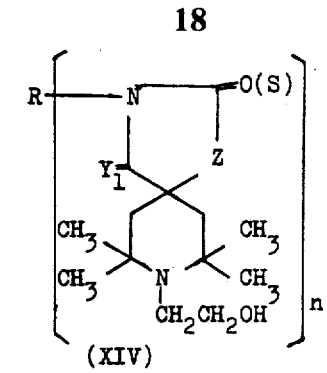

(XIV)

In the above formulae, R, n, $Y_1$ and Z are as defined above.

This method will be more fully exemplified by Example 9 and provide, for example, those compounds designated by Nos. 17 and 18 hereinabove.

7. The compound (XV) is reacted with ethylene oxide by heating under pressure in the presence of an acid to produce the compound (XVI).

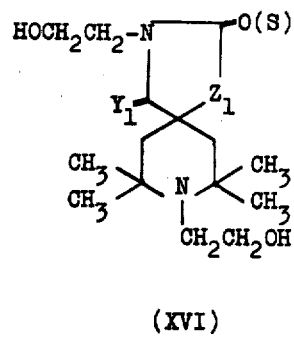

(XV)

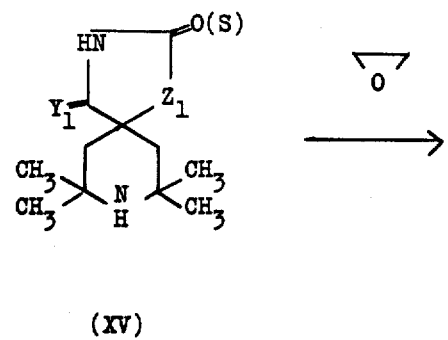

(XVI)

In the above formulae, $Y_1$ and $Z_1$ are as defined above.
This method will be more fully exemplified by Example 10 and provide, for example, the compound designated by No. 39 hereinabove.

8. The compound (XVII) or (XIX) is reacted with the acid halide in the presence of a base to produce the compound (XVIII) or (XX).

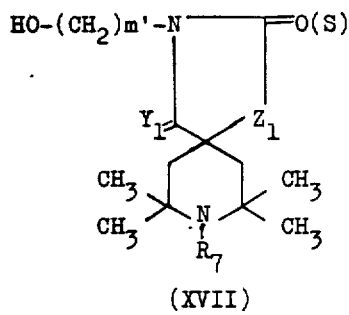

(XVII)

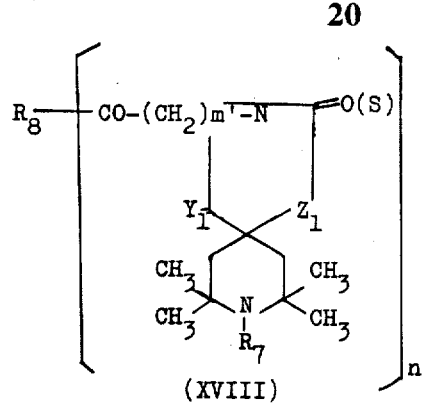

(XVIII)

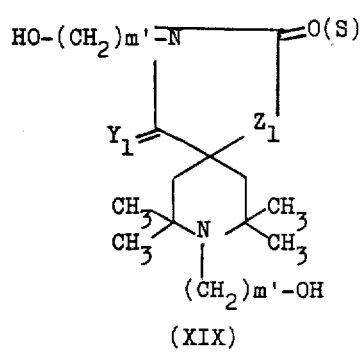

(XIX)

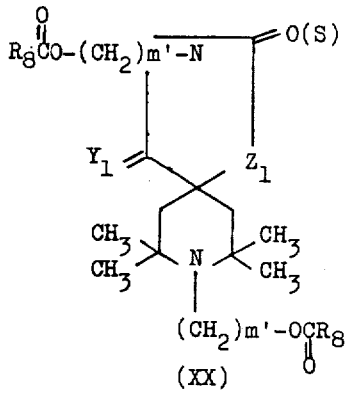

(XX)

In the above formulae, $n$, $X_1$, $Y_1$ and $Z_1$ are as defined above, the acyl moiety of the acyl halide $R_8$—$(COX_1)_n$ or $R_8COX_1$ represents a monoacyl group, a biacyl group, a triacyl group or tetraacyl group, $R_7$ represents an alkyl group, allyl group, 2-propynyl group, a cyanoalkyl group, an alkoxyalkyl group, an alkenyloxyalkyl group, an aryloxyalkyl group, an epoxyalkyl group, an alkoxycarbonylalkyl group, an aralkyl group, an acyl group or nitroso group and $m^1$ is an integer of 2 through 4 inclusive.

This method will be more fully exemplified by Example 11 and provide, for example, those compounds designated by Nos. 46, 47, 48, 49, 50, 51, 52, 53, 54, 55, 121, 122, 125, 126 and 129 hereinabove.

9. The compound (XXI) or the alkali metal salt thereof is reacted with the halide $[R_9(X_1)_n]$ to produce the compound In the above formulae, $n$, $X_1$ and $Z_1$ are as defined above. $R_8$ represents, when $n$ is 1, an alkyl group, allyl group, 2-propynyl group, a hydroxyalkyl group, a cyanoalkyl group, an alkoxyalkyl group, an alkenyloxyalkyl group, an aryloxyalkyl group, an epoxyalkyl group, an acyloxyalkyl group, an alkylthioalkyl group, an alkoxycarbonylalkyl group, an aryloxycarbonylalkyl group, an aralkyl group, an alkoxycarbonyl group, an aralkyloxycarbonyl group, a substituted phosphino group or a substituted phosphinyl group; when n is 2, an alkylene group, an alkenylene group, an aralkylene group, a bisacyloxyalkylene group, an alkylenebisoxycarbonylalkyl group or a dialkyleneether group; when $n$ is 3, an alkanetriyl group, a trisacyloxyalkylene group, an alkanetris(oxycarbonylalkyl) group or the group

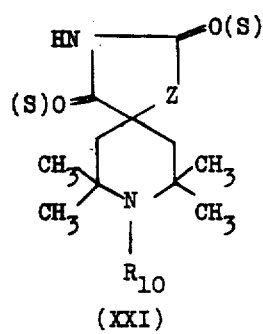

(XXI)

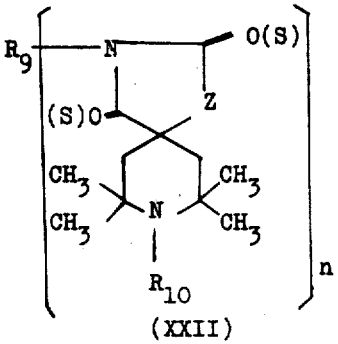

(XXII)

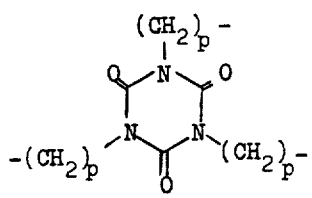

in which *p* is as defined above; and, when *n* is 4, an alkanetertrayl group, a tetrakis(acyloxyalkylene) group or an alkanetetrakis(oxycarbonylalkyl) group. $R_{10}$ represents an alkyl group, a cyanoalkyl group, an alkoxyalkyl group, an acyl group, an aralkyloxycarbonyl group or nitroso group.

This method will be more fully exemplified by Example 12 and provide, for example, those compounds designated by Nos. 21, 22, 23, 24, 25, 26, 32, 41, 49, 56, 58, 60, 61, 62, 63, 65, 80, 100, 101, 127 and 130 hereinabove. (10) The compound (XXIII) is subjected to reduction to produce the compound (XXIV).

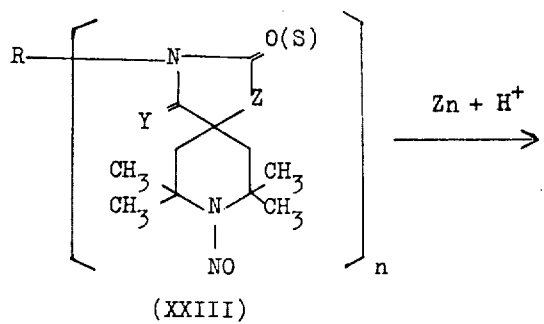

(XXIII)

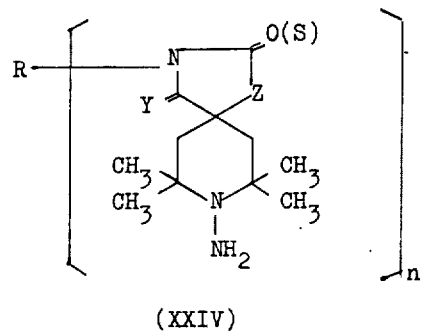

(XXIV)

In the above formulae, R, n, Y and Z are as defined above.

This method will be more fully exemplified by Example 13 and provide, for example, the compound designated by No. 27 hereinabove.

11. The compound (XXIV) is reacted with the acid halide ($R_8COX_1$) in the presence of a base to produce the compound (XXV).

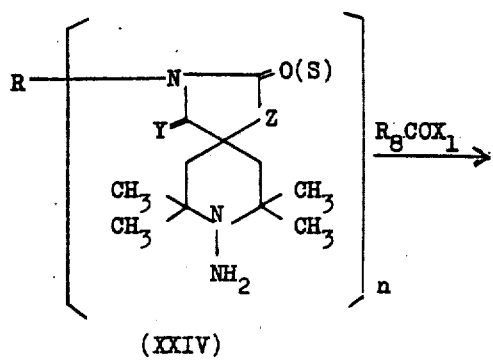

(XXIV)

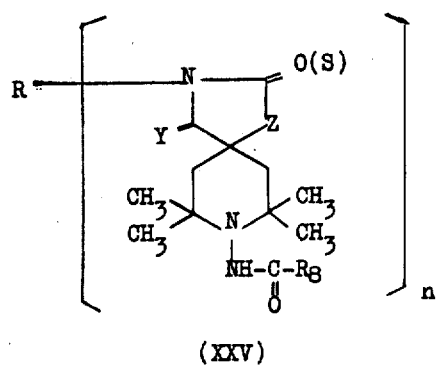

(XXV)

In the above formulae, R, *n*, $X_1$, Y, the group $R_8CO$ and Z are as defined above.

This method will be more fully exemplified by Example 14 and provide, for example, the compound designated by No. 28 hereinabove.

12. The compound (XXIV) is reacted with the halide ($R_{11}X$) in the presence of a base to produce the compound (XXVI).

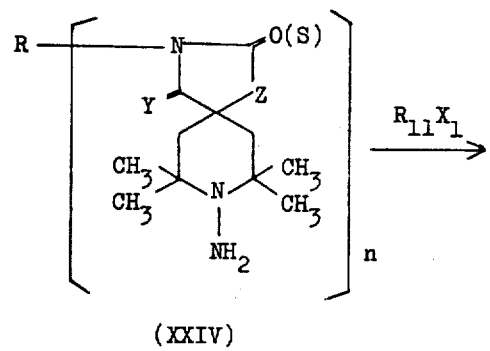

(XXIV)

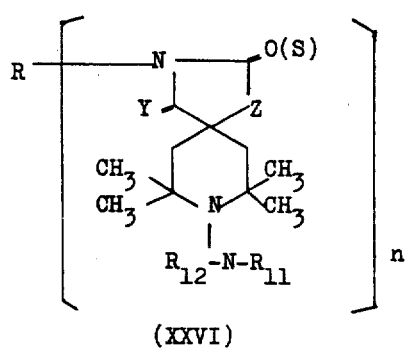

(XXVI)

In the above formulae, R, *n*, $X_1$, Y and Z are as defined above, $R_{11}$ represents an alkyl group and $R_{12}$ represents hydrogen atom or an alkyl group.

This method will be more fully exemplified by Example 15 and provide, for example, the compound designated by No. 29 hereinabove.

13. The compound (XXVI) is reacted with dialkyl sulfate by heating to produce the compound (XXVII).

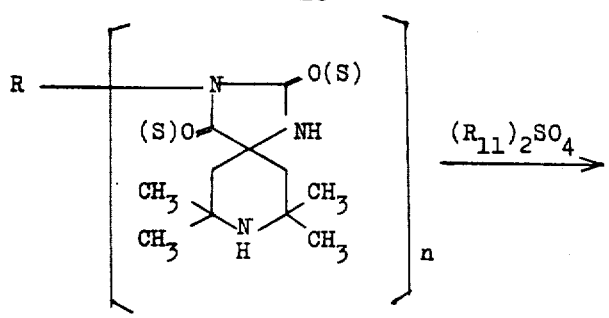

(XXVI)

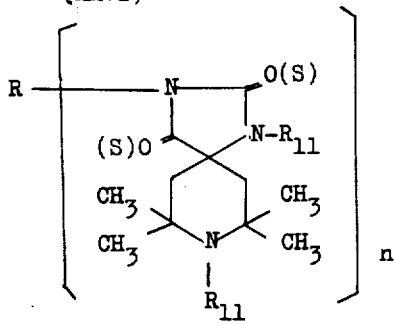

(XXVII)

In the above formulae, R, $R_{11}$ and n are as defined above.

This method will be more fully exemplified by Example 16 and provide, for example, those compounds designated by Nos. 8, 19, 66, 70, 71, 102, 104, 108, 110 and 112 hereinabove.

In still another aspect of this invention, there is provided a synthetic polymer composition stabilized against photo- and thermal-deterioration which contains at least one of the new piperidine derivatives (I) having incorporated therein.

The piperidine derivatives (I) employed as a stabilizer in the present invention may be readily incorporated into the synthetic polymers by any of the various standard procedures commonly utilized in the art. The stabilizer may be incorporated into the synthetic polymers at any desired stage prior to the manufacture of shaped articles therefrom. Thus, for example, the stabilizer in the form of a dry powder may be admixed with the synthetic polymer, or a suspension or emulsion of the stabilizer may be admixed with a solution, suspension or emulsion of the synthetic polymer.

The amount of the piperidine derivatives (I) employed in the synthetic polymer in accordance with the present invention may be varied widely, depending upon the types, properties and particular uses of the synthetic polymer to be stabilized. In general, the piperidine derivatives of the formula (I) may be added in an amount ranging from 0.01 to 5.0% by weight, based on the amount of the synthetic polymer, but the practical range is varied depending upon the type of the synthetic polymer, that is 0.01 to 2.0% by weight, preferably 0.02 to 1.0% by weight for polyolefins, 0.01 to 1.0% by weight, preferably 0.02 to 0.5% by weight for polyvinyl chloride and polyvinylidene chloride, and 0.01 to 5.0% by weight, preferably 0.02 to 2.0% by weight fo polyurethanes and polyamides.

The present stabilizer may be used alone or in combination with other known antioxidants, ultraviolet absorbents, fillers, pigments and the like.

If desired, two or more of the present stabilizers i.e. the piperidine derivatives of the formula (I) may also be satisfactorily used in this invention.

In order that the invention may be better understood, the following Examples are given solely for the purpose of illustration of this invention. In the Examples, all parts are given by weight unless otherwise indicated and the number of the test compound as used hereinbelow is the same as illustratively shown above.

Examples 1 through 16 describe the preparation of some representative compounds of the piperidine derivative (I) of this invention.

Examples 17 through 29 describe the synthetic polymer compositions having incorporated therein the piperidine derivatives (I) and their stabilizing effects.

EXAMPLE 1

1,3,8-Triaza-3,8-dibenzyl-7,7,9,9-tetramethyl-spiro[4.5]decane-2,4-dione

To a suspension of 22.5 g. of 1,3,8-triaza-7,7,9,9-tetramethyl-spiro[4.5]decane-2,4-dione in 300 ml. of ethanol was added 6.2 g. of potassium hydroxide and the resulting mixture was heated under reflux for 1 hour. After cooling, acetone was added to the reaction mixture, thereby separating crystalline substance, which was then recovered by filtration to give the potassium salt of the above starting material.

To 5 g. of the potassium salt obtained above was added 30 g. of benzyl chloride and the resulting mixture was heated under reflux for 20 hours. After cooling, the reaction mixture was poured into a 10% aqueous solution of sodium hydroxide and crystalline substance so separated was recovered by filtration and recrystallized from benzene to give the desired product as white crystals melting at 262°–263°C.

Analysis for $C_{25}H_{31}N_3O_2$: Calculated: C, 74.10%; H, 7.65%; N, 10.37%. Found: C, 74.33%; H, 7.66%, N, 10.28%. Mass spectrum: $M^+$ m/e 405 (Calculated 405).

EXAMPLE 2

1,3,8-Triaza-7,7,9,9-tetramethyl-3,8-di(2-propynyl)-spiro[4.5]decane-2,4-dione

To a mixture of 2.6 g. of potassium salt of 1,3,8-triaza-7,7,9,9-tetramethyl-spiro[4.5]decane-2,4-dione, 2.6 g. of 2-propynyl bromide and 1.4 g. of potassium carbonate was added 20 ml. of dimethylformamide and the resulting mixture was heated at 80°–90°C. for 15 hours. After completion of the reaction, the reaction mixture was concentrated and the concentrate was extracted with benzene. The benzene extract was again concentrated and the residual crystalline substance was recrystallized from aqueous ethanol to give the desired product as white crystals melting at 198°–200°C.

Analysis for $C_{17}H_{23}N_3O_2$: Calculated: C, 67.75%; H, 7.69%; N, 13.94%. Found: C, 67.70%; H, 7.73%; N, 13.89%.

EXAMPLE 3

8-Allyl-1,3,8-triaza-7,7,9,9-tetramethyl-3-n-octyl-spiro[4.5]decane-2,4-dione

To a mixture of 17 g. of 1,3,8-triaza-7,7,9,9-tetramethyl-3-n-octyl-spiro[4.5]decane-2,4-dione and 16 g. of allyl chloride were added 20 ml. of triethylamine and 20 ml. of dimethylformamide. The resulting mixture was heated under reflux for 20 hours.

After completion of the reaction, the reaction mixture was concentrated, the residue was washed with an 10% aqueous potassium carbonate solution and extracted with benzene. The benzene extract was subjected to a column chromatography on alumina and the resulting crystalline substance was recrystallized from n-hexane to give the desired product as white crystals melting at 123°–124°C.

Analysis for $C_{22}H_{39}N_3O_2$: Calculated: C, 70.00%; H, 10.35%; N, 11.15%. Found: C, 69.74%; H, 10.40%; N, 11.39%.

EXAMPLE 4

1,3,8-Triaza-8-benzyl-7,7,9,9-tetramethyl-3-n-octyl-spiro[4.5]decane-2,4-dione

A mixture of 2 g. of 1,3,8-triaza-7,7,9,9-tetramethyl-3-n-octyl-spiro[4.5]decane-2,4-dione, 10 g. of benzyl chloride and 1 g. of potassium carbonate was heated under reflux for 15 hours. After cooling, the reaction mixture was added to an 10% aqueous potassium carbonate solution and extracted with benzene. The benzene solution so obtained was washed with water, dried over anhydrous sodium sulfate and then concentrated. The residual crystalline substance was recrystallized from petroleum ether to give the desired product as white crystals melting at 167°–168°C.

Analysis for $C_{26}H_{41}N_3O_2$: Calculated: C, 73.02%; H, 9.66%; N. 9.83%. Found: C, 72,83%; H, 9.53%; N, 10.00%. IR spectrum (Nujol mull): $\nu_{NH}$ 3380, $\nu_{C=O}$ 1780, 1713 cm$^{-1}$. Mass spectrum M$^+$ m/e 567. (Calculated: 567)

EXAMPLE 5

1,3,8-Triaza-3-butyl-8-(2,3-epoxypropyl)-7,7,9,9-tetramethylspiro [4.5]decane-2,4-dione A solution of 20.0 g. of 1,3,8-triaza-3-butyl-7,7,9,9-tetramethyl-spiro [4.5]decane-2,4-dione in 40 g of epichlorohydrin was refluxed with stirring for 15 hours. After completion of the reaction, excess epichlorohydrin was removed by distillation under reduced pressure and the residue was dissolved in 200 ml. of ether. The resulting solution was washed with an 20% aqueous solution of potassium carbonate and then with water. After drying over anhydrous sodium sulfate, the ether was distilled off to give the desired product as crude crystalline substances which were then recrystallized from ethyl acetate, thereby yielding the desired product in pure state as white crystals melting at 125°–128°C.

Analysis for $C_{17}H_{27}N_3O_3$: Calculated: C, 63.52% H, 8.47%; N, 13.07%. Found: C, 63.49%; H, 8.51%; N, 13.15%.

EXAMPLE 6

1,3,8-Triaza-1,3,8-tribenzyl-7,7,9,9-tetramethyl-spiro[4.5]decane-2,4-dione

To 2 g. of 1,3,8-triaza-3,8-dibenzyl-7,7,9,9-tetramethylspiro[4.5]decane-2,4-dione were added 1 g of sodium hydride and 40 ml of xylene and the resulting mixture was heated under reflux for 5.5 hours. Then, 5.25 g. of benzyl chloride was added to the mixture and the mixture so obtained was heated under reflux for further 10 hours. After cooling, insoluble materials were filtered off from the reaction mixture and the filtrate was concentrated. To the residue was added 10% aqueous hydrochloric acid and the resulting mixture was washed with ether. The aqueous layer was separated from the organic layer and neutralized by addition of potassium carbonate followed by extraction with benzene. The benzene extract was concentrated and the residual crystalline substance was recrystallized from n-hexane to give the desired product as white crystals melting at 135°–136°C.

Analysis for $C_{32}H_{37}N_3O_2$: Calculated: C, 77.54%; H, 7.52%; N, 8.48%. Found: C, 77.42%; H, 7.91%; N, 8.50%.

EXAMPLE 7

4,4'-Bis[1,3,8-triaza-7,7,9,9-tetramethyl-2-oxo-8-(2-propynyl)4-(2-propynylimino)-spiro[4.5]-3-decyl]diphenylmethane To a mixture of 1 g. of 4,4'-bis(1,3,8-triaza-4-imino7,7,9,9-tetramethyl-2-oxo-spiro-[4.5]-3-decyl) diphenylmethane, 0.9 g. of 2-propynyl bromide and 1 g. of sodium carbonate was added 10 ml. of dimethylformamide and the resulting mixture was heated at 140°–150°C. for 12 hours. After completion of the reaction, the dimethylformamide was distilled off, the residue was washed with water and then benzene and finally recrystallized from dimethylformamide to give the desired product as pale yellow crystals not melting at 250°C.

Analysis for $C_{47}H_{56}N_8O_2$: Calculated: C, 73.79%; H, 7.38%; N, 14.65%. Found: C, 73.86%; H, 7.45%; N, 14.54%. IR spectrum (Nujol mull): $\nu_{NH}$ 3300 cm$^{-1}$, $\nu_{C=O}$ 2100 cm$^{-1}$; $\nu_{C=O}$ 1720 cm$^{-1}$, $\nu_{C=N}$ 1675 cm$^{-1}$

EXAMPLE 8

1,3,8-Triaza-3-butyl-7,7,8,9,9-pentamethyl-spiro[4.5]-decane-2,4-dione

To 281 g. of 1,3,8-triaza-3-butyl-7,7,9,9-tetramethyl-spiro[4.5]decane-2,4-dione was added 256 g. of 90% formic acid and to the resulting mixture was added dropwise at 20°–30°C. over 1 hour 162 g. of 37% formaldehyde. After completion of the dropwise addition, the mixture so obtained was refluxed with stirring by gradual heating for about 7 hours, at the end of which evolution of gaseous carbon dioxide ceased.

After completion of the reaction, the reaction mixture was colled, diluted with 800 ml. of water and then neutralized to a pH of 9 to 9.5 with an 45% aqueous sodium hydroxide solution. Crystalline substances thus separated were recovered by filtration, washed with water and dried. Recrystallization from methanol gave the desired product as white crystals melting at 135°–137°C.

Analysis for $C_{16}H_{29}N_3O_2$: Calculated: C, 65.05%; H, 9.89%; N, 14.22%. Found: C, 65.05%; H, 9.93%; N, 14.21%.

EXAMPLE 9

1,3,8-Triaza-8-hydroxyethyl-7,7,9,9-tetramethyl-3-n-octylspiro[4.5]decane-2,4-dione Into a sealed tube were charged 5.7 g. of 1,3,8-triaza7,7,9,9-tetramethyl-3-n-octyl-spiro[4.5]decane-2,4-dione, 25 ml. of methanol and 0.1 ml. of hydrichloric acid. Then, 1.7 g. of ethylene oxide was added thereto. The tube was sealed and heated at 103°C. for 3 hours. After completion of the reaction, the reaction mixture was concentrated and the residue was recrystallized from ligroin to give the desired product as white crystals melting at 138°–139°C.

Analysis for $C_{21}H_{39}N_3O_3$: Calculated: C, 66.11%; H, 10.30%; N, 11.01%. Found: C, 65.99%; H, 10.55%; N, 10.91%.

EXAMPLE 10

1,3,8-Triaza-3,8-bis(2-hydroxyethyl)-7,7,9,9-tetramethyl-spiro[4.5]decane-2,4-dione A mixture of 4.5 g. of 1,3,8-triaza-7,7,9,9-tetramethylspiro[4.5]decane-2,4-dione, 20 ml. of methanol, and 0.2 g. of hydrochloric acid was charged into a sealed tube. To the tube was then charged 5 g. of ethylene oxide. After sealing the tube, the mixture was heated at 110°C. for 5 hours. After completion of the reaction, insoluble substances were filtered off and the filtrate was concentrated. The residue was recrystallized from a mixture of methanol and ether to give the desired product as colorless needles melting at 188°–190°C.

Analysis for $C_{15}H_{27}N_3O_4$: Calculated: C, 57.51%; H, 8.69%; N, 13.42%. Found: C, 57.63%; H, 8.55%; N, 13.40%.

EXAMPLE 11

1,3,8-Triaza-3,8-bis(2-p-chlorobenzyloxyethyl)-7,7,9,9-tetramethyl-spiro[4.5]decane-2,4-dione To a suspension of 2.5 g. of 1,3,8-triaza-3,8-bis(2-hydroxyethyl)-7,7,9,9-tetramethyl-spiro[4.5]decane-2,4-dione and 3.3 g. of potassium carbonate in 30 ml. of benzene was added 4.4 g. of p-chlorobenzoyl chloride at room temperature. The resulting mixture was stirred at that temperature for 2 hours and heated under reflux for additional 2 hours. After cooling, the reaction mixture was washed with water, dried over anhydrous sodium sulfate and the benzene was distilled off. The residue so obtained was recrystallized from ethyl acetate to give the desired product as white crystals melting at 202°–202.5°C.

Analysis for $C_{29}H_{33}N_3O_6Cl$: Calculated: C, 58.98%; H, 5.59%; N, 7.11%; Cl, 12.01%. Found: C, 58.69%; H, 5.80%; N, 6.89%; Cl, 12.36%. IR spectrum (Nujol mull): $\nu_{C=O}$ 1768, 1729, 1710 cm$^{-1}$.

EXAMPLE 12

1,3,8-Triaza-3-(2,3-epoxypropyl)-7,7,8,9,9-pentamethyl-spiro[4.5]decane-2,4-dione In 100 ml. of water was dissolved 2.4 g. of sodium hydroxide and to the resulting solution was added with stirring 12.0 g. of 1,3,8-triaza-7,7,8,9,9-pentamethyl-spiro[4.5]decane-2,4-dione to form the corresponding sodium salt in situ. To the mixture was then added 0.56 g. of epichlorohydrin and the resulting mixture was stirred at room temperature for 60 hours. The crystalline substance separated in situ was recovered by filtration and washed with water to give the desired product as crude crystals, which were then dissolved in 150 ml. of toluene with heating and impurities were filtered off and the filtrate was cooled to give the desired product as white crystals melting at 174°–176°C.

Analysis for $C_{15}H_{25}N_3O_3$: Calculated: C, 60.99%; H, 8.53%; N, 14.23%. Found: C, 60.77%; H, 8.42%; N, 14.45%.

EXAMPLE 13

8-Amino-1,3,8-triaza-3-butyl-7,7,9,9-tetramethyl-spiro[4.5]decane-2,4-dione

To 9.3 g. of 1,3,8-traza-3-butyl-7,7,9,9-tetramethyl-8-nitroso-spiro[4.5]decane-2,4-dione were added 11.2 g. of zinc powder and 35 ml. of water and to the resulting mixture was added 25 ml. of 85% acetic acid. The mixture so obtained was heated at 60°–65°C. for 1.5 hours. After cooling, sodium hydroxide was added to the reaction mixture, which was then extracted with benzene. The benzene extract was dried over anhydrous sodium sulfate and concentrated. The residue was recrystallized from petroleum benzine to give the desired product as white crystals melting at 154°–156°C.

Analysis for $C_{15}H_{28}N_4O_2$: Calculated: C, 60.78%; H, 9.52%; N, 18.90%. Found: C, 60.50%; H, 9.57%; N, 18.69%. IR spectrum (Nujol mull): $\nu_{C=O}$ 1770, 1708 cm$^{-1}$.

EXAMPLE 14

1,3,8-Triaza-8-benzamido-3-butyl-7,7,9,9-tetramethyl-spiro[4.5]decane-2,4-dione

To a solution of 2 g. of 8-amino-1,3,8-triaza-3-butyl7,7,9,9-tetramethyl-spiro[4.5]decane-2,4-dione and 2 g. of triethylamine in 50 ml. of benzene was added 1.2 g. of benzoyl chloride and the resulting mixture was stirred at 40°–50°C. for 5 hours. After completion of the reaction, the reaction mixture was concentrated and to the residue was added water followed by filtration. The crystalline substances so separated were recrystallized from benzene to give the desired product as white crystals melting at 235°–236°C.

Analysis for $C_{22}H_{32}N_4O_3$: Calculated: C, 65.97%; H, 8.05%; N, 13.99%. Found: C, 65.61%; H, 7.99%; N, 13.94%. IR spectrum (Nujol mull): $\nu_{C=O}$ 1762, 1710, 1690 cm$^{-1}$.

EXAMPLE 15

1,3,8-Triaza-3-butyl-8-ethylamino-7,7,9,9-tetramethyl-spiro[4.5]decane-2,4-dione To a solution of 0.45 g. of 8-amino-1,3,8-triaza-3-butyl-7,7,9,9-tetramethyl-spiro[4.5]-decane-2,4-dione and 2 g. of potassium carbonate in 10 ml. of dimethylformamide was added 1 g. of ethyl iodide and the resulting mixture was heated at 100°–105°C. for 8 hours. After completion of the reaction, the reaction mixture was concentrated and to the residue was added water followed by filtration. The crystalline substances so separated were recrystallized from petroleum benzine to give the desired product as white crystals melting at 138°–139°C.

Analysis for $C_{17}H_{32}N_4O_2$: Calculated: C, 62.93%; H, 9.94%; N, 17.27%. Found: C, 63.20%; H, 10.09%; N, 17.01%. Mass spectrum: M$^+$324 (Calculated Molecular Weight 324.46).

EXAMPLE 16

1,6-Bis(1,3,8-triaza-1,7,7,8,9,9-hexamethyl-2,4-dioxospiro[4.5]-3-decyl)hexane

To a solution of 2.66 g. of 1,6-bis(1,3,8-triaza-7,7,9,9-tetramethyl-2,4-dioxo-spiro[4.5]-3-decyl)hexane and 3.2 g. of sodium hydroxide in 50 ml. of dioxane was added 5 g. of dimethyl sulfate and the resulting mixture was heated at 60°–65°C. for 3 hours. After completion of the reaction, the reaction mixture was concentrated and the residue was extracted with benzene. The benzene extract was washed with water, dried over anhydrous sodium sulfate and then concentrated. The residue was recrystallized from petroleum benzine to give the desired product as white crystals melting at 125°–126°C.

Analysis for $C_{32}H_{56}N_6O_4$: Calculated: C, 65.27%; H, 9.59%; N, 14.27%. Found: C, 65.57%; H, 9.55%; N, 13.95%. IR spectrum (Nujol mull): $\nu_{C=O}$ 1762, 1700 cm$^{-1}$.

By utilizing any suitable procedure of those set forth in the above Examples, the following compounds were prepared:

1,3,8-triaza-3,7,7,8,9,9-hexamethyl-spiro[4.5]decane-2,4-dione (m.p. 209°–210°C.), 1,3,8-triaza-7,7,8,9,9-pentamethyl-3-octyl-spiro[4.5]decane-2,4-dione (m.p. 127°–128°C.), 1,3,8-triaza-3,8-diethyl-7,7,9,9-tetramethyl-spiro[4.5]decane-2,4-dione (m.p. 162°–164°C.), 1,3,8-triaza-3-butyl-8-ethyl-7,7,9,9-tetramethyl-spiro[4.5]decane-2,4-dione (m.p. 105°–107°C.), 1,3,8-triaza-8-ethyl-7,7,9,9-tetramethyl-3-octyl-spiro[4.5]decane-2,4-dione (m.p. 137°–138°C.), 1,3,8-triaza-1,3,7,7,8,9,9-heptamethyl-spiro[4.5]-decane-2,4-dione (m.p. 81°–82°C.), 1,3,8-triaza-3-butyl-1,8-diethyl-7,7,9,9-tetramethyl-spiro[4.5]decane-2,4-dione (colorless liquid after chromatography), 1,3,8-triaza-1-butyl-8-ethyl-7,7,9,9-tetramethyl-3-octyl-spiro[4.5]decane-2,4-dione (b.p. 195°–200°C./3mmHg.), 3,8-diaza-7,7,8,9,9-pentamethyl-3-octadecyl-1-oxa-spiro[4.5]decane-2,4-dione (m.p. 83°–84°C.), 1,3,8-traza-8-benzyl-7,7,9,9-tetramethyl-3-octadecyl-spiro[4.5]decane-2,4-dione (m.p. 111°–113°C.), 1,3,8-triaza-3,7,7,8,9,9-hexamethyl-1-ethoxymethyl-spiro[4.5]decane-2,4-dione (b.p. 161°–162°C./0.9mmHg.), 1,3,8-triaza-3,7,7,8,9,9-hexamethyl-1-(2-phenoxyethyl)-spiro[4.5]decane-2,4-dione (m.p. 92°–93°C.), 1,3,8-triaza-3,7,7,8,9,9-hexamethyl-1-(2-vinyloxyethyl)-spiro[4.5]decane-2,4-dione (b.p. 171°–172°C./0.9mmHg.), 1,3,8-triaza-3-butyl-8-(2-hydroxyethyl)-7,7,9,9-tetramethylspiro[4.5]decane-2,4-dione (m.p. 112°–114°C.), 1,3,8-triaza-8-(2-cyanoethyl)-1,3,7,7,9,9-hexamethyl-spiro[4.5]decane-2,4-dione (m.p. 23°–26°C.), 1,3,8-triaza-8-(2-ethoxyethyl)-3,7,7,9,9-pentamethyl-spiro[4.5]decane-2,4-dione (m.p. 135°–136°C.), 1,3,8-triaza-8-cinnamoyl-3,7,7,9,9-pentamethyl-spiro[4.5]decane-2,4-dione (m.p. 279°–280°C.), 1,3,8-triaza-3,7,7,9,9-pentamethyl-8-nitroso-spiro[4.5]decane-2,4-dione (m.p. 228°–229°C.), 1,3,8-triaza-3-butyl-7,7,9,9-tetramethyl-8-nitroso-spiro[4.5]decane-2,4-dione (m.p. 131°–132°C.), 3-allyl-1,3,8-triaza-7,7,8,9,9-pentamethyl-spiro[4.5]decane-2,4-dione (m.p. 137°–139°C.), 3-allyl-1,3,8-triaza-8-ethyl-7,7,9,9-tetramethyl-spiro[4.5]decane-2,4-dione (m.p. 166°–167°C.), 1,3-diallyl-1,3,8-triaza-7,7,8,9,9-pentamethyl-spiro[4.5]decane-2,4-dithione (b.p. 174°–176°C./3mmHg.), 3,8-diallyl-1,3,8-triaza-7,7,9,9-tetramethyl-spiro[4.5]decane-2,4-dione (m.p. 154°–155°C.), 3,8-diallyl-1,3,8-triaza-1-benzyl-7,7,9,9-tetramethyl-spiro[4.5]decane-2,4-dione (b.p. 205°–207°C./1mmHg.), 3-allyl-1,3,8-triaza-8-(2,3-epoxypropyl)-7,7,9,9-tetramethylspiro[4.5]decane-2,4-dione (m.p. 162°–164°C.), 3-allyl-1,3,8-triaza-8-benzyl-7,7,9,9-tetramethyl-spiro[4.5]decane-2,4-dione (m.p. 189°–190°C.), 1,3,8-triaza-8-(2,3-epoxypropyl)-7,7,9,9-tetramethyl-3-(2-propynyl)-spiro[4.5]decane-2,4-dione (m.p. 193.5°–196.5°C.), 1,3,8-triaza-8-cyanomethyl-3-(3-hydroxypropyl)-7,7,9,9-tetramethyl-spiro[4.5]decane-2,4-dione (m.p. 191°–192°C.), 1,3,8-triaza-1,7,7,9,9-pentamethyl-3,8-bis(2-methoxyethyl)-spiro[4.5]decane-2,4-dione (m.p. 34°–36°C.), 1,3,8-triaza-3-ethoxymethyl-7,7,8,9,9-pentamethyl-spiro[4.5]decane-2,4-dione (m.p. 176°–177°C.), 1,3,8-triaza-8-ethyl-7,7,9,9-tetramethyl-3-(2-vinyloxyethyl)-spiro[4.5]decane-2,4-dione (m.p. 149°–150°C.), 8-allyl-1,3,8-triaza-7,7,9,9-tetramethyl-3-(2-phenoxyethyl)-spiro[4.5]decane-2,4-dione (m.p. 175°–176°C.), 3-(2-acetoxyethyl)-1,3,8-triaza-8-benzyl-7,7,9,9-tetramethylspiro[4.5]decane-2,4-dione (m.p. 191°–191.5°C.), 3,8-bis(2-acetoxyethyl)-1,3,8-triaza-7,7,9,9-tetramethylspiro[4.5]decane-2,4-dione (m.p. 149°–150°C.), 1,3,8-triaza-2,2,6,6-tetramethyl-3,8-bis(2-octanoyloxyethyl)-spiro[4.5]decane-2,4-dione (m.p. 69°–70°C.), 8-acryloyl-3-(2-acryloyloxyethyl)-1,3,8-triaza-7,7,9,9-tetramethyl-spiro[4.5]decane-2,4-dione (m.p. 173°–174°C.), 3,8-bis(2-acryloyloxyethyl)-1,3,8-triaza-7,7,9,9-tetramethylspiro[4.5]decane-2,4-dione (m.p. 119°–120°C.), 1,3,8-triaza-3-(2-benzoyloxyethyl)-8-ethyl-7,7,9,9-tetramethyl-spiro[4.5]decane-2,4-dione (m.p. 166°–167°C.), 1,3,8-triaza-3,8-bis(2-benzoyloxyethyl)-7,7,9,9-tetramethylspiro[4.5]decane-2,4-dione (m.p. 187°–188.5°C.), 1,3,8-triaza-7,7,9,9-tetramethyl-3,8-bis(2-m-toluoyloxyethyl)-spiro[4.5]decane-2,4-dione (m.p. 152°–153°C.), 3,8-bis(2-o-anisoyloxyethyl)-1,3,8-triaza-7,7,9,9-tetramethylspiro[4.5]decane-2,4-dione (m.p. 141°–142°C.), 1,3,8-triaza-3,8-bis(2-cyanoethyl)-7,7,9,9-tetramethyl-spiro[4.5]decane-2,4-dione (m.p. 126°–127°C.)

1,3,8-triaza-7,7,8,9,9-pentamethyl-3-(2-methylthioethyl)spiro[4.5]decane-2,4-dione (m.p. 138°–139°C.), 1,3,8-triaza-3,8-bis(2,3-epoxypropyl)-7,7,9,9-tetramethylspiro[4.5]decane-2,4-dione (m.p. 164.5°–166.5°C.), 1,3,8-triaza-3-ethoxycarbonylmethyl-7,7,8,9,9-pentamethylspiro[4.5]decane-2,4-dione (m.p. 145°–146°C.), 1,3,8-triaza-3-ethoxycarbonyl-7,7,8,9,9-pentamethyl-spiro[4.5]decane-2,4-dione (m.p. 133°–134°C.), 1,3,8-triaza-3-benzyl-7,7,8,9,9-pentamethyl-spiro[4.5]-decane-2,4-dione (m.p. 206°–208.5°C.), 1,3,8-triaza-3-benzyl-7,7,9,9-tetramethyl-8-octyl-spiro[4.5]-decane-2,4-dione (m.p. 175°–176°C.), 1,3,8-triaza-3-benzyl-1,8-diethyl-7,7,9,9-tetramethyl-spiro[4.5]decane-2,4-dione (colorless liquid after chromatography), 1,3,8-triaza-1,3-dibenzyl-7,7,8,9,9-pentamethyl-spiro[4.5]decane-2,4-dithione (m.p. 101°–102°C.), 1,3,8-triaza-7,7,9,9-tetramethyl-3-phenethyl-8-(2-propynyl)-spiro[4.5]decane-2,4-dione (m.p. 194°–195°C.), 1,3,8-triaza-3,8-dibenzyl-1,7,7,9,9-pentamethylspiro[4.5]decane-2,4-dione (m.p. 132°–133°C.), 1,3,8-triaza-3,8-dibenzyl-1-butyl-7,7,9,9-tetramethyl-spiro[4.5]decane-2,4-dione (m.p. 133.5°–134°C.), 1-(2-acetoxyethyl)-1,3,8-triaza-3,8-dibenzyl-7,7,9,9-tetramethylspiro[4.5]decane-2,4-dione (colorless liquid after chromatography), 1,3,8-triaza-1-(2-benzoyloxyethyl)-3,8-dibenzyl-7,7,9,9-tetramethyl-spiro[4.5]decane-2,4-dione (colorless liquid after chromatography), 1,3,8-triaza-3,8-dibenzyl-7,7,9,9-tetramethyl-1-(2-propynyl)spiro[4.5]decane-2,4-dione (m.p. 123.5°–124.5°C.), 1,3,8-triaza-3-benzyl-8-(2,3-epoxypropyl)-7,7,9,9-tetramethylspiro[4.5]decane-2,4-dione (m.p. 197°–199.5°C.), 1,3,8-triaza-7,7,8,9,9-pentamethyl-3-(p-methylbenzyl)-spiro[4.5]decane-2,4-dione (m.p. 162°–163°C.), 1,3,8-triaza-3-(p-chlorobenzyl)-7,7,8,9,9-pentamethyl-spiro[4.5]decane-2,4-dione (m.p. 170.5°–171.5°C.), 8-acryloyl-1,3,8-triaza-3-benzyl-7,7,9,9-tetramethyl-spiro[4.5]decane-2,4-dione (m.p. 131°–132°C.), 1,3,8-triaza-3-cyclohexyl-7,7,8,9,9-pentamethyl-spiro[4.5]decane-2,4-dione (m.p. 186°–188°C.), 1,3,8-triaza-3-cyclohexyl-8-(2,3-epoxypropyl)-7,7,9,9-tetramethylspiro[4.5]decane-2,4-dione (m.p. 179°–182.5°C.), 1,3,8-triaza-8-benzyl-3-cyclohexyl-7,7,9,9-tetramethyl-spiro[4.5]decane-2,4-dione (m.p. 237°–238°C.), 1,3,8-triaza-8-benzyl-4-benzylimino-3-cyclohexyl-7,7,9,9-tetramethyl-spiro[4.5]decane-2-one (m.p. 203°–204°C.), 1,3,8-triaza-7,7,8,9,9-pentamethyl-3-phenyl-spiro[4.5]decane-2,4-dione (m.p. 156°C.), 1,3,8-triaza-8-(2,3-epoxypropyl)-7,7,9,9-tetramethyl-3-phenylspiro[4.5]decane-2,4-dione (m.p. 179°–182.5°C), 1,3,8-triaza-4-imino-7,7,8,9,9-pentamethyl-3-phenyl-spiro[4.5]decane-2-one (m.p. 140°–141°C.), 1,3,8-triaza-7,7,8,9,9-pentamethyl-4-methylimino-3-phenyl-spiro[4.5]decane-2-one (m.p. 204°C.), 1,3,8-triaza-4-imino-7,7,8,9,9-pentamethyl-3-phenyl-spiro[4.5]decane-2-thione (m.p. 140°–142°C.), 8-allyl-4-allylimino-1,3,8-triaza-7,7,9,9-tetramethyl-3-phenyl-spiro[4.5]decane-2-one (m.p. 120°–121°C.), 1,3,8-triaza-8-(2-hydroxyethyl)-4-(2-hydroxyethylimino)-7,7,9,9-tetramethyl-3-phenyl-spiro[4.5]decane-2-one (m.p. 225°–diphenylmethane C.), 1,3,8-triaza-1,7,7,9,9-pentamethyl-8-(2-methoxyethyl)-4-(2-methoxyethylimino)-3-phenyl-spiro[4.5]decane-2-one (m.p. 131°–132°C.), 1,3,8-triaza-1,8-dibenzyl-7,7,9,9-tetramethyl-3-phenyl-spiro[4.5]decane-4-one-2-thione(m.p. 202°–203°C.), 3,8-diaza-4-imino-7,7,8,9,9-pentamethyl-3-(α-naphthyl)-1-oxa-spiro[4.5]decane-2-thione (m.p. >260°C.), 1,3,8-triaza-8-benzyl-7,7,9,9-tetramethyl-3-(p-tolyl)-spiro[4.5]decane-2,4-dione (m.p. 259°–260°C.), 3,8-diaza-7,7,8,9,9-pentamethyl-1-oxa-3-(p-tolyl)-spiro[4.5]decane-2,4-dione (m.p. 166°–167°C.), 3,8-diaza-4-imino-7,7,8,9,9-pentamethyl-1-oxa-3-(p-tolyl)-spiro[4.5]decane-2-one (m.p. 163°–164°C.), 3,8-diaza-3-(o-chlorophenyl)-7,7,8,9,9-pentamethyl-1-oxa-spiro[4.5]decane-2,4-dione (m.p. 190°–191°C.), 3,8-diaza-3-(o-chlorophenyl)-7,7,8,9,9-pentamethyl-4-methylimino-1-oxa-spiro[4.5]decane-2-one (m.p. 181°–182°C.), 1,3,8-triaza-7,7,8,9,9-pentamethyl-3-diphenoxyphosphinyl-spiro[4.5]decane-2,4-dithione (m.p. 176°–177°C.), 1,3-bis(1,3,8-triaza-1,7,7,8,9,9-hexamethyl-2,4-dioxo-spiro[4.5]-3-decyl)propane (m.p. 117°–118°C.), 1,6-bis(1,3,8-triaza-7,7,8,9,9-pentamethyl-2,4-dioxo-spiro[4.5]-3-decyl)hexane (m.p. 231°–234°C.), 1,6-bis[1,3,8-triaza-7,7,9,9-tetramethyl-2,4-dioxo-8-(2-propynyl)-spiro[4.5]-3-decyl]hexane (m.p. 231°–232°C.), 1,6-bis[1,3,8-triaza-8-(2,3-epoxypropyl)-7,7,9,9-tetramethyl-2,4-dioxo-spiro[4.5]-3-decyl]hexane (m.p. 263.5°–268.5°C.), 1,6-bis(1,3,8-triaza-8-benzyl-7,7,9,9-tetramethyl-2,4-dioxospiro[4.5]-3-decyl)hexane (m.p. 281°–283°C.), 1,4-bis(1,3,8-triaza-1,7,7,8,9,9-hexamethyl-2,4-dioxo-spiro[4.5]-3-decyl)-trans-2-butene (m.p. 175°–177°C.), 2,2'-bis(1,3,8-triaza-7,7,8,9,9-pentamethyl-2,4-dioxo-spiro[4.5]-3-decyl)diethylether (m.p. 235°–236°C.), 2,2'-bis(1,3,8-triaza-1,7,7,8,9,9-hexamethyl-2,4-dioxo-spiro[4.5]-3-decyl)diethylether (m.p. 92°–93°C.), α,α'-bis(1,3,8-triaza-7,7,8,9,9-pentamethyl-2,4-dioxo-spiro[4.5]-3-decyl)-p-xylene (m.p. 293°–295°C.), α,α'-bis(1,3,8-triaza-1,7,7,8,9,9-hexamethyl-2,4-dioxo-spiro[4.5]-3-decyl)-p-xylene (m.p. 197°–199°C.), α,α'-bis[1,3,8-triaza-8-(2,3-epoxypropyl)-7,7,9,9-tetramethyl-2,4-dioxo-spiro[4.5]-3-decyl]-p-xylene (m.p. 254°–258°C.), α,α'-bis(1,3,8-triaza-8-benzyl-7,7,9,9-tetramethyl-2,4-dioxospiro[4.5]-3-decyl)-p-xylene (m.p. >300°C), 2,4-bis(1,3,8-triaza-7,7,8,9,9-pentamethyl-2,4-dioxo-spiro[4.5]-3-decyl)toluene (m.p. >300°C.), 2,4-bis(3,8-diaza-4-imino-7,7,8,9,9-pentamethyl-1-oxa-2-oxo-spiro[4.5]-3-decyl)toluene (m.p. 243°–245°C.), 4,4'-bis(1,3,8-triaza-7,7,8,9,9-pentamethyl-2,4-dioxo-spiro[4.5]-3-decyl)diphenylmethane (m.p. 238°–242.5°C.), 4,4'-bis[1,3,8-triaza-8-(2,3-epoxypropyl)-7,7,9,9-tetramethyl-2,4-dioxo-spiro[4.5]-3-decyl]diphenylmethane (m.p. 232°–236°C.), bis[2-(1,3,8-triaza-7,7,8,9,9-pentamethyl-2,4-dioxospiro[4.5]-3-decyl)ethyl]adipate (m.p. 206°–210°C.), bis[2-(1,3,8-triaza-7,7,8,9,9-pentamethyl-2,4-dioxospiro[4.5]-3-decyl)ethyl]terephthalate (m.p. 272°–273°C.), tris[2-(1,3,8-triaza-7,7,8,9,9-pentamethyl-2,4-dioxospiro[4.5]-3-decyl)ethyl]trimellitate (m.p. 289°–292°C. with decomposition), 2,2',2''-tris[1,3,8-triaza-8-(2,3-epoxypropyl)-7,7,9,9-tetramethyl-2,4-dioxo-spiro[4.5]-3-decyl]triethylisocyanurate (m.p. 215°–220°C.), tetrakis[2-(1,3,8-triaza-7,7,8,9,9-pentamethyl-2,4-dioxospiro[4.5]-3-decyl)ethyl]pyromellitate (m.p. >250°C.) and pentaerythritol tetrakis(1,3,8-triaza-7,7,8,9,9-pentamethyl-2,4-dioxo-spiro[4.5]-3-decylmethylcarboxylate) (m.p. 250°C.).

EXAMPLE 17

Into 100 parts of polypropylens ["Noblen JHH-G," trade name, available from Mitsui Toatsu Chemicals Inc., Japan, employed after twice recrystallizations from monochlorobenzene] was incorporated 0.25 part of each of the test compounds of this invention indicated below. The resulting mixture was mixed and melted and then molded into a sheet having a thickness of 0.5 mm. under heating and pressure.

As a control, the polypropylene sheet was prepared in a similar manner to that described above without any of stabilizers for comparative purpose.

Then, all of these sheets thus formed were tested for the brittleness time (which means the time, expressed in terms of hour, until the test sheet will become brittle) under ultraviolet ray irradiation at a temperature of 45°C. by means of the fade meter prescribed in Japanese Industrial Standard JIS-1044 entitled "Testing Method of Color Fastness to Light of Dyed Textiles and Dyestuffs," Paragraph 3.8 (in English).

The results are given in the following Table 1.

Table 1

| Test compound No. | Brittleness time (hour) | Test compound No. | Brittleness time (hour) |
|---|---|---|---|
| 1 | 760 | 32 | 420 |
| 2 | 800 | 33 | 920 |
| 3 | 820 | 34 | 980 |
| 4 | 700 | 35 | 800 |
| 5 | 680 | 36 | 900 |
| 6 | 1060 | 37 | 680 |
| 7 | 800 | 38 | 740 |
| 8 | 620 | 39 | 660 |
| 9 | 1280 | 40 | 700 |
| 10 | 220 | 42 | 780 |
| 11 | 1100 | 43 | 680 |
| 12 | 1020 | 44 | 640 |
| 13 | 1120 | 45 | 680 |
| 14 | 580 | 46 | 600 |
| 15 | 500 | 47 | 840 |
| 16 | 620 | 48 | 660 |
| 17 | 640 | 49 | 580 |
| 18 | 880 | 50 | 700 |
| 19 | 720 | 51 | 620 |
| 20 | 800 | 52 | 560 |
| 21 | 480 | 53 | 520 |
| 22 | 540 | 54 | 640 |
| 23 | 520 | 55 | 500 |
| 25 | 460 | 56 | 640 |
| 26 | 520 | 57 | 420 |
| 27 | 440 | 58 | 1420 |
| 28 | 580 | 59 | 1160 |
| 29 | 620 | 60 | 620 |
| 30 | 940 | 63 | 540 |
| 31 | 800 | 64 | 620 |
| 65 | 520 | 96 | 280 |
| 66 | 560 | 97 | 240 |
| 67 | 360 | 98 | 240 |
| 68 | 480 | 99 | 260 |
| 69 | 740 | 101 | 380 |
| 70 | 820 | 102 | 940 |
| 71 | 660 | 103 | 820 |
| 72 | 740 | 104 | 980 |
| 73 | 620 | 105 | 620 |
| 74 | 680 | 106 | 940 |
| 75 | 660 | 107 | 840 |
| 76 | 1080 | 108 | 600 |
| 77 | 720 | 109 | 880 |
| 78 | 680 | 110 | 880 |
| 79 | 580 | 111 | 580 |
| 80 | 660 | 112 | 820 |
| 81 | 740 | 113 | 820 |
| 82 | 620 | 114 | 920 |
| 83 | 800 | 115 | 580 |
| 84 | 580 | 116 | 460 |
| 85 | 540 | 117 | 560 |
| 86 | 660 | 118 | 980 |
| 87 | 500 | 119 | 500 |
| 88 | 560 | 120 | 860 |
| 89 | 320 | 121 | 680 |
| 90 | 480 | 122 | 520 |
| 91 | 460 | 126 | 640 |
| 92 | 540 | 128 | 1020 |
| 93 | 640 | 129 | 720 |
| 94 | 220 | 130 | 800 |
| 95 | 780 | | |
| None | | | 100 |

EXAMPLE 18

Into 100 parts of high-density polyethylene ["Hi-Zex," trade name, available from Mitsui Toatsu Chemicals Inc., Japan, employed after twice recrystallizations from toluol] were incorporated 0.25 part of each of the test compounds of this invention indicated below. The resulting mixture was made into a sheet by the same procedure as in the above Example 17.

The sheet thus formed was tested for the brittleness time by the same test method as in the above Example 17. The results are given in the following Table 2.

Table 2

| Test compound No. | Brittleness time (hour) | Test compound No. | Brittleness time (hour) |
|---|---|---|---|
| 1 | 1360 | 21 | 840 |
| 2 | 1880 | 22 | 880 |
| 3 | 1720 | 23 | 820 |
| 4 | 1320 | 25 | 1080 |
| 5 | 1400 | 26 | 1160 |
| 6 | 2500 | 27 | 860 |
| 7 | 2320 | 28 | 1220 |
| 8 | 1240 | 29 | 1300 |
| 9 | 2660 | 30 | 1980 |
| 10 | 580 | 31 | 1820 |
| 11 | 2480 | 32 | 920 |
| 12 | 2280 | 33 | 1900 |
| 13 | 1960 | 34 | 2020 |
| 14 | 1020 | 35 | 2100 |
| 15 | 920 | 36 | 1920 |
| 16 | 1140 | 37 | 1580 |
| 17 | 1360 | 38 | 1280 |
| 18 | 1900 | 39 | 1300 |
| 19 | 1540 | 40 | 1480 |
| 20 | 1800 | 42 | 1660 |
| 43 | 1520 | 81 | 1280 |
| 44 | 1440 | 82 | 1140 |
| 45 | 1500 | 83 | 1760 |
| 46 | 1320 | 84 | 960 |
| 47 | 2040 | 85 | 960 |
| 48 | 1260 | 86 | 1180 |
| 49 | 1220 | 87 | 820 |
| 50 | 1280 | 88 | 980 |
| 51 | 1200 | 89 | 760 |
| 52 | 1040 | 90 | 820 |
| 53 | 1000 | 91 | 780 |
| 54 | 1260 | 92 | 920 |
| 55 | 980 | 93 | 1180 |
| 56 | 1140 | 94 | 540 |
| 57 | 860 | 95 | 1580 |
| 58 | 2800 | 96 | 600 |
| 59 | 2080 | 97 | 560 |
| 60 | 1100 | 98 | 500 |
| 63 | 960 | 99 | 560 |
| 64 | 1020 | 101 | 660 |
| 65 | 900 | 102 | 2280 |
| 66 | 1100 | 103 | 1360 |
| 67 | 780 | 104 | 2300 |
| 68 | 860 | 105 | 1120 |
| 69 | 1300 | 106 | 1580 |
| 70 | 2080 | 107 | 1400 |
| 71 | 1120 | 108 | 1080 |
| 72 | 1220 | 109 | 1800 |
| 73 | 1140 | 110 | 1760 |
| 74 | 1200 | 111 | 1020 |
| 75 | 1080 | 112 | 1440 |
| 76 | 2100 | 113 | 1580 |
| 77 | 2040 | 114 | 1820 |
| 78 | 1240 | 115 | 1100 |
| 79 | 1060 | 116 | 800 |
| 80 | 1040 | 117 | 1080 |
| 118 | 1640 | 126 | 1140 |
| 119 | 960 | 128 | 1880 |
| 120 | 1680 | 129 | 1300 |
| 121 | 1320 | 130 | 1440 |
| 122 | 940 | | |
| None | | | 400 |

EXAMPLE 19

A number of sheets prepared in the above Examples 17 and 18 were aged under the following aging condition to determine the brittleness time.

Aging test

Aging at 120°C. for the polypropylene and 125°C. for the polyethylene in a Geer's aging tester prescribed in Japanese Industrial Standard JIS-K-6301 entitled "Physical Testing Methods for Vulcanized Rubber," Paragraph 6.5 (in English).

The results are given in the following Table 3.

Table 3

| Test compound No. | Brittleness time (hour) | |
|---|---|---|
| | Polypropylene | High-density polyethylene |
| 20 | 220 | 240 |
| 35 | 240 | 300 |
| 38 | 280 | 360 |
| 58 | 1320 | 840 |
| 59 | 432 | 408 |
| 77 | 400 | 380 |
| 86 | 320 | 340 |
| 102 | 960 | 620 |
| 104 | 824 | 680 |
| 110 | 744 | 628 |
| 112 | 720 | 504 |
| 118 | 808 | 552 |
| 128 | 950 | 600 |
| None | not more than 20 | 40 |

EXAMPLE 20

Into 100 parts of polystyrene ["Styron 666," trade name, available from Asahi-Dow Limited, Japan] was incorporated 0.25 part of each of the test compounds of this invention indicated below. The resulting mixture was made into a sheet having the thickness of 0.5 mm. as shown in the above Example 17.

The sheet thus formed was placed in a fade meter under ultraviolet ray irradiation at a temperature of 45°C. for 100 hours.

Then, infrared spectrum of the sheet was compared at 1700 cm$^{-1}$ to determine the increase in a number of carbonyl group.

The results are given in the following Table 4.

Table 4

| Test compound No. | Increase in absorbancy 1700 cm$^{-1}$ |
|---|---|
| 1 | 5 |
| 2 | 4 |
| 3 | 4 |
| 7 | 5 |
| 11 | 4 |
| 12 | 3 |
| 35 | 3 |
| 47 | 3 |
| 58 | 3 |
| 59 | 3 |
| 69 | 5 |
| 76 | 3 |
| 77 | 3 |
| 104 | 3 |
| 112 | 3 |
| 114 | 4 |
| 117 | 4 |
| None | 13 |

EXAMPLE 21

Into 100 parts of polyvinyl chloride ["Geon-103 EP," trade name, available from The Japanese Geon Co., Ltd., Japan] were incorporated 30 parts of ABS resin ["ABS 60," trade name, available from The Japan Synthetic Rubber Co., Ltd., Japan], 3 parts of tribasic lead sulfate, 2 parts of dibasic lead phosphate, 2 parts of lead stearate and 1 part of each of the test compounds of this invention indicated below. The resulting mixture was blended and kneaded for 8 minutes on a kneading roll at 160°C. and then formed into a sheet having a thickness of about 0.5 mm. The sheet was subjected to the exposure to ultraviolet ray for 50 hours and then tested for the retention of ultimate elongation and ultimate tensile strength according to a conventional method.

The results are given in the following Table 5.

Table 5

| Test compound No. | Retention of ultimate elongation (%) | Retention of ultimate tensile strength(%) |
|---|---|---|
| 3 | 55 | 88 |
| 7 | 52 | 87 |
| 11 | 65 | 91 |
| 12 | 61 | 86 |
| 20 | 63 | 90 |
| 33 | 66 | 93 |
| 50 | 53 | 89 |
| 69 | 57 | 87 |
| 76 | 59 | 87 |
| 106 | 63 | 91 |
| 114 | 60 | 92 |
| None | 42 | 82 |

EXAMPLE 22

Into 100 parts of polyvinyl chloride ["Geon 103," trade name, available from The Japanese Geon Co., Ltd., Japan] were incorporated 1 part of lead stearate, 0.5 part of dibasic lead phosphite, 0.5 part of barium stearate, 0.5 part of cadmium stearate and 0.2 part of each of the test compounds of this invention indicated below. The resulting mixture was blended and kneaded for 4 minutes on a kneading roll at 180°C. and then formed into a sheet having a thickness of 0.5 mm. The sheet was tested for the discoloration degree thereof by the aging test method set forth below.

Aging test

1. Exposure to the sunshine carbon apparatus prescribed in Japanese Industrial Standard JIS Z-0230 entitled "Accelerated Weathering test of Rust Proofing Oils", Paragraph 2 for 600 hours.

2. The sheet was aged for 90 minutes at 170°C. in the Geer's aging tester prescribed in the above Example 19. The results are given in the following Table 6.

Table 6

| Test compound No. | Sunshine carbon apparatus after 600 hours | Geer's aging tester after 90 minutes, 170°C |
|---|---|---|
| 2 | yellow | pale yellow |
| 7 | '' | '' |
| 11 | '' | '' |
| 12 | pale yellow | '' |
| 33 | yellow | yellow |
| 58 | pale yellow | pale yellow |
| 69 | '' | '' |
| 76 | '' | '' |
| 114 | '' | '' |
| None | dark brown | black |

EXAMPLE 23

Into 100 parts of 6-nylon ["CM 1011," trade name, available from Toray Industries Inc., Japan, containing no stabilizer] was incorporated 0.25 part of each of the test compounds of this invention indicated below. The resulting mixture was heated and melted and then molded into a film having a thickness of about 0.1 mm. under pressure. The film thus formed was aged under the following aging condition and thereafter subjected to a tensile test to determine the retentions of ultimate tensile strength and ultimate elongation by a standard method.

Aging test

1. Exposure to ultraviolet ray for 200 hours in the fade meter described above at 45°C.
2. The sheet was aged for 2 hours at 160°C. in the Geer's aging tester prescribed in the above Example 19.

The results are given in the following Table 7.

Table 7

| Test compound No. | Fade meter, 200 hours | | Geer's aging tester, 2 hours, 160°C | |
|---|---|---|---|---|
| | Retention of ultimate elongation | Retention of ultimate tensile strength | Retention of ultimate elongation | Retention of ultimate tensile strength |
| 1 | 47 | 68 | 73 | 79 |
| 7 | 51 | 70 | 74 | 78 |
| 11 | 32 | 62 | 77 | 72 |
| 12 | 83 | 72 | 70 | 77 |
| 18 | 62 | 68 | 68 | 73 |
| 20 | 78 | 70 | 81 | 72 |
| 33 | 55 | 60 | 63 | 65 |
| 58 | 83 | 78 | 87 | 77 |
| 69 | 96 | 76 | 70 | 75 |
| 76 | 91 | 73 | 72 | 78 |
| 107 | 86 | 74 | 78 | 70 |
| None | 18 | 55 | 31 | 71 |

EXAMPLE 24

Into 100 parts of polyurethane prepared from polycaprolactone ["E-5080," trade name, available from The Nippon Elastollan Industries Ltd., Japan] was incorporated 0.5 part of each of the test compounds of this invention indicated below. The resulting mixture was heated and melted and then molded into a sheet having a thickness of about 0.5 mm. The sheet thus formed was subjected to the exposure to ultraviolet ray for 15 hours in the fade meter as specified in the above Example 17 at 45°C. and then tested for the retentions of ultimate elongation and ultimate tensile strength as in the above Example 21.

The results are given in the following Table 8.

Table 8

| Test compound No. | Retention of ultimate elongation | Retention of ultimate tensile strength |
|---|---|---|
| 3 | 100 | 95 |
| 8 | 92 | 88 |
| 11 | 88 | 76 |
| 12 | 91 | 90 |
| 20 | 89 | 78 |
| 30 | 87 | 83 |
| 33 | 90 | 88 |
| 47 | 86 | 75 |
| 58 | 97 | 91 |
| 69 | 94 | 97 |
| 76 | 90 | 92 |
| 107 | 97 | 94 |
| 117 | 88 | 92 |
| None | 86 | 56 |

EXAMPLE 25

Into 100 parts of polyacetal resin ["Delrin 500," trade name, available from Showa Neoprene K. K., Japan] was incorporated 0.5 part of each of the test compounds of this invention indicated below. The resulting mixture was heated and melted at 220°C.

The film thus formed was aged by heating at 222°C. in air for 30 minutes to determine the reduction in weight of the film.

The results are given in the following Table 9.

Table 9

| Test compound No. | Reduction in weight at 222°C. after 30 minutes (%) |
|---|---|
| 1 | 0.33 |
| 8 | 0.45 |
| 11 | 0.38 |
| 13 | 0.24 |
| 35 | 0.34 |
| 58 | 0.30 |
| 69 | 0.34 |
| 70 | 0.35 |
| 76 | 0.31 |
| 104 | 0.35 |
| None | 0.77 |

EXAMPLE 26

Into 100 parts of polyester resin ["Ester-G13," trade name, available from Mitsui Toatsu Chemicals, Inc., Japan] were incorporated 1 part of benzoyl peroxide and 0.2 part of each of the test compounds of this invention indicated below. The resulting mixture was mixed and pre-heated at 60°C. for 30 minutes. Then, the pre-heated mixture was cured by heating at 100°C. for 1 hour to form into a plate having a thickness of 3 mm.

The plate thus formed was subjected to the exposure to the sunshine carbon apparatus for 60 hours and then the coloration degree thereof was determined.

The results are given in the following Table 10.

Table 10

| Test compound No. | Sunshine carbon apparatus (Hunter colori and gloss meter) color difference Δ E |
|---|---|
| 3 | 3.7 |
| 11 | 3.2 |
| 13 | 2.4 |
| 20 | 2.5 |
| 33 | 2.8 |
| 52 | 3.6 |
| 58 | 2.8 |
| 76 | 2.9 |
| 104 | 3.7 |
| None | 4.5 |

EXAMPLE 27

Into 100 parts of polyvinylidene chloride resin ["Kureharon DOA," trade name, available from Kureha Chemical Industry Co., Japan] was incorporated 0.1 part of each of the test compounds of this invention indicated below. The resulting mixture was dissolved in an appropriate amount of tetrahydrofuran and the solvent was distilled off to form a sheet having a thickness of about 0.5 mm.

The sheet thus formed was subjected to the exposure to ultraviolet ray irradiation in the fade meter at 45°C. for 5 hours and the coloration degree thereof was determined and compared.

The results are given in the following Table 11.

Table 11

| Test compound No. | Coloration degree in fade meter after 5 hours |
|---|---|
| 1 | pale yellow |
| 12 | " |
| 13 | " |
| 20 | " |
| 58 | " |
| 70 | yellow |
| 77 | " |
| None | brown |

EXAMPLE 28

Into 100 parts of polyethylene ["2100 GP," trade name, available from Mitsui Toatsu Chemicals Inc., Japan] were incorporated 0.25 part of each of the test compounds of this invention indicated below and 0.5 part of BHT (2,6-di-tert.butyl-hydroxy toluene). The resulting mixture was heated and melted and then molded into a plate having a thickness of 3 mm.

The plate thus formed was left in a dark place at 60°C. for 3 weeks and then the coloration degree thereof was determined.

The results are given in the following Table 12.

Table 12

| Test compound No. (+ BHT) | After 3 weeks at 60°C. |
|---|---|
| 11 | Colorless |
| 12 | " |
| 13 | " |
| 33 | " |
| 58 | " |
| 59 | " |
| 69 | " |
| 76 | " |
| 109 | " |
| 111 | " |

EXAMPLE 29

The substantially same procedure as shown in the above Example 28 was repeated except that polypropylene ["JHH-G," trade name, available from Mitsui Toatsu Chemicals Inc., Japan, employed after twice recrystallization from monochlorobenzene] was utilized instead of the polyethylene.

The results are given in the following Table 13.

Table 13

| Test compound No. (+ BHT) | After 4 weeks at 60°C. |
|---|---|
| 11 | Colorless |
| 12 | " |
| 13 | " |
| 33 | " |
| 58 | " |
| 59 | " |
| 69 | " |
| 76 | " |
| 109 | " |
| 111 | " |

It can be apparent from the above-given results that the piperidine derivatives (I) of this invention exert a high degree of stabilizing effect against thermal- and photo-deterioration of various synthetic polymers.

What is claimed is:

1. A synthetic polymer composition stabilized against photo- and thermal-deterioration wherein there is incorporated, in a sufficient amount to prevent said deterioration, a compound having the formula $$\left[ R - \underset{R'}{\underset{|}{N}} \begin{array}{c} X \\ Y \\ Z \end{array} \right]_n \qquad (I)$$

wherein
R' represents an alkyl group, a substituted alkyl group, an acyl group, an alkoxycarbonyl group, a substituted alkoxycarbonyl group, an amino group, a substituted amino group or nitroso group;
X represents oxygen atom or sulfur atom;
Y represents oxygen atom, sulfur atom or a group of the formula = N—R" in which R" is hydrogen atom, an alkyl group or a substituted alkyl group;
Z represents oxygen atom or a group of the formula > N—R'" in which R'" is hydrogen atom, an alkyl group or a substituted alkyl group;
n is an integer of 1 through 4 inclusive; and
R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group,
when n is 2, an alkylene group, an alkenylene group, an arylene group, a substituted arylene group, an aralkylene group, an alkylenediphenylene group, a bis-(acyloxyalkylene) group, an alkylenebis-(oxycarbonylalkyl) group, a dialkylene ether group or a diphenylene ether group,
when n is 3, an alkanetriyl group, a tris-(acyloxyalkylene) group, an alkane-tris-(oxycarbonylalkyl) group or a group of the group $$-(CH_2)_p - \underset{O}{\overset{(CH_2)_p-}{\underset{\|}{N}}}\underset{\|}{\overset{O}{\underset{\|}{N}}}(CH_2)_p-$$

in which p is an integer of 1 through 8 inclusive and p's may be the same or different, and,
when n is 4, an alkane tetrayl group, a tetrakis-(acyloxyalkylene) group or an alkanetetrakis(oxycarbonylalkyl) group.

2. The synthetic polymer composition according to claim 1 wherein said compound (I) is a member selected from the compounds (I) in which
R' represents an alkyl group of 1 to 20 carbon atoms, a hydroxyalkyl group, an allyl group, 2-propynyl group, a cyanoalkyl group, an alkoxyalkyl group, an alkenyloxyalkyl group, an aryloxyalkyl group, an alkylthioalkyl group, an epoxyalkyl group, an acyloxyalkyl group, an alkoxycarbonylalkyl group, an aralkyl group, an acryloyl group, an acryloyl group which is substituted with alkyl or phenyl, an aralkyloxycarbonyl group, an amino group or an amino group which is substituted with aroyl or alkyl;
R represents, when n is 1, the above-defined alkyl group, a phenyl or naphthyl group which may be substituted with halogen or alkyl in the aryl moiety, a cycloalkyl group, an alkoxycarbonyl group, an aralkyloxycarbonyl group, the group of the formula $$\langle\!\!\!\bigcirc\!\!\!\rangle - O - \overset{\|}{P} - O - \langle\!\!\!\bigcirc\!\!\!\rangle$$

or the group of the formula

41

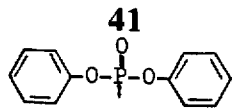

when $n$ is 2, a polymethylene group of 1 to 10 carbon atoms, a group of the formula $-(CH_2)_p-CH=CH-(CH_2)_p-$ in which $p$ is an integer of 1 through 8 inclusive and $p$'s may be the same or different, a phenylene group which may be substituted with alkyl, a group of the formula

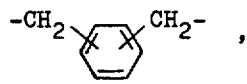

a group of the formula

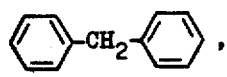

a group of the formula

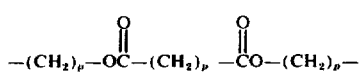

in which $p$ is as defined above and $p_1$ is an integer of zero through 8 inclusive, a group of the formula

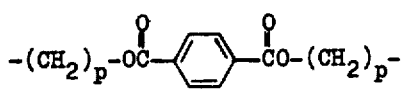

in which $p$ is as defined above, a group of the formula

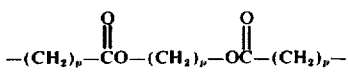

in which $p$ is as defined above, a group of the formula $-(CH_2)_p-O-(CH_2)_p-$
in which $p$ is as defined above or a group of the formula

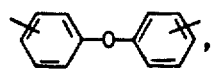

when $n$ is 3, a group of the formula

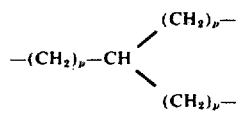

in which $p$ is as defined above, a group of the formula

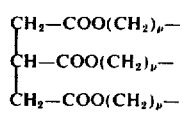

42 in which $p$ is as defined above, a group of the formula

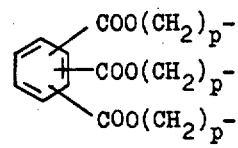

in which $p$ is as defined above, a group of the formula

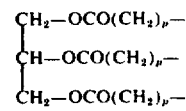

in which $p$ is as defined above or a group of the formula

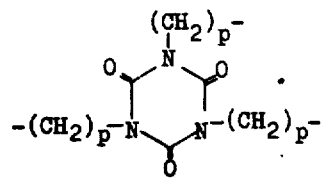

in which p is as defined above, and, when n is 4, a group of the formula

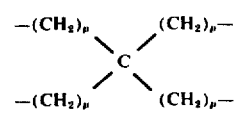

in which $p$ is as defined above, a group of the formula

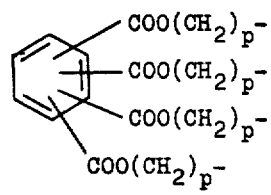

in which $p$ is as defined above or a group of the formula

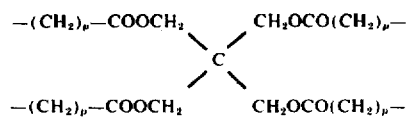

in which p is as defined above, p's being optionally the same or different.

3. The synthetic polymer composition according to claim 1 wherein said compound (I) is a member selected from the compounds (I) in which R' represents an alkyl group, allyl group, an aralkyl group, an acyloxyalkyl group, a hydroxyalkyl group or 2,3-epoxypropyl group;

X and Y represent oxygen atom;

Z represents a group of the formula > N-R''' in which R''' is hydrogen atom or an alkyl group;

n is an integer of 1 or 2; and

R represents, when n is 1, an alkyl group, allyl group, an aralkyl group, an acyloxyalkyl group or 2,3-epoxypropyl group, and, when n is 2, an alkylene group, a group of the formula

or a group of the formula $-(CH_2)_p-O-(CH_2)_p$, in which p is an integer of 1 through 8 inclusive.

4. The synthetic polymer composition according to claim 1 wherein said compound (I) is incorporated in the amount of 0.01 - 5.0% by weight, based upon the amount of the synthetic polymer.

5. The synthetic polymer composition according to claim 1 wherein said polymer is a polyolefin.

6. The synthetic polymer composition according to claim 1 wherein said polymer is a polyvinyl chloride.

7. The synthetic polymer composition according to claim 1 wherein said polymer is a polyurethane.

8. The synthetic polymer composition according to claim 1 wherein said polymer is a polyamide.

9. The synthetic polymer composition according to claim 1 wherein said polymer is a polyacetal.

10. The synthetic polymer composition according to claim 1 wherein said polymer is a polyester.

11. The synthetic polymer composition according to claim 1 wherein said compound (I) is selected from the group consisting of, 1,3,8-triaza-3-butyl-7,7,8,9,9-pentamethyl-spiro[4.5]decane-2,4-dione, 1,3,8-triaza-7,7,8,9,9-pentamethyl-3-octyl-spiro[4.5]decane-2,4-dione, 8-allyl-1,3,8-triaza-7,7,9,9-tetramethyl-3-octyl-spiro[4,5]-decane-2,4-dione, 1,3,8-triaza-8-benzyl-7,7,9,9-tetramethyl-3-octyl-spiro[4.5]-decane-2,4-dione, 1,3,8-triaza-8-(2-hydroxyethyl)-7,7,9,9-tetramethyl-3-octyl-spiro[4.5]decane-2,4-dione, 1,3,8-triaza-3-butyl-8-(2,3-epoxypropyl)-7,7,9,9-tetramethyl-spiro[4.5]decane-2,4-dione, 3-allyl-1,3,8-triaza-7,7,8,9,9-pentamethyl-spiro[4.5]decane-2,4-dione, 3,8-diallyl-1,3,8-triaza-7,7,9,9-tetramethyl-spiro[4.5]decane-2,4-dione, 3-allyl-1,3,8-triaza-8-(2,3-epoxypropyl)-7,7,9,9-tetramethyl-spiro[4.5]decane-2,4-dione, 3,8-bis(2-acetoxyethyl)-1,3,8-triaza-7,7,9,9-tetramethyl-spiro[4.5]decane-2,4-dione, 1,3,8-triaza-3-(2,3-epoxypropyl)-7,7,8,9,9-pentamethyl-spiro[4.5]decane-2,4-dione, 1,3,8-triaza-3,8-bis(2,3-epoxypropyl)-7,7,9,9-tetramethyl-spiro[4.5]decane-2,4-dione, 1,3,8-triaza-3,8-dibenzyl-1,7,7,9,9-pentamethyl-spiro[4.5]decane-2,4-dione, 1,3-bis(1,3,8-triaza-1,7,7,8,9,9-hexamethyl-2,4-dioxo-spiro[4.5]-3-decyl)propane, 1,6-bis(1,3,8-triaza-1,7,7,8,9,9-hexamethyl-2,4-dioxo-spiro[4.5]-3-decyl)hexane, 2,2'-bis(1,3,8-triaza-7,7,8,9,9-pentamethyl-2,4-dioxo-spiro[4.5]-3-decyl)diethylether, 2,2'-bis(1,3,8-triaza-1,7,7,8,9,9-hexamethyl-2,4-dioxo-spiro[4.5]-3-decyl)diethylether, 1,3,8-triaza-1,3,7,7,8,9,9-heptamethyl-spiro[4.5]-decane-2,4-dione and α,α'-bis(1,3,8-triaza-1,7,7,8,9,9-hexamethyl-2,4-dioxo-spiro[4.5]-3-decyl)-p-xylene.

12. A synthetic polymer composition stabilized against photo- and thermal-deterioration wherein there is incorporated, in a sufficient amount to prevent said deterioration, a compound having the formula

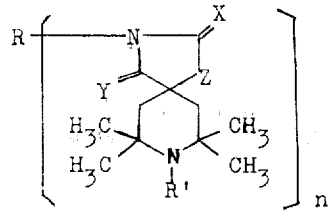

wherein

R' is alkyl;

X and Y represent oxygen;

Z represents a group of the formula >N-R'''
in which R''' is hydrogen;

n is 1, and

R is alkyl.

13. A synthetic polymer composition stabilized against photo- and thermal-deterioration wherein there is incorporated, in a sufficient amount to prevent said deterioration, a compound having the formula

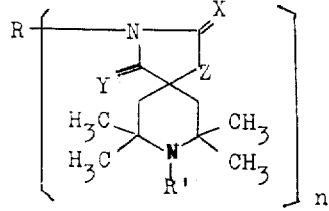

wherein

R' represents an alkyl group, an alkenyl group, an aralkyl group, an acyloxyalkyl group, a hydroxyalkyl group or an epoxyalkyl group;

X and Y represent oxygen;

Z represents a group of the formula >N-R'''
in which R''' is a hydrogen atom or an alkyl group;

n is 1, and

R represents an alkyl group, an alkenyl group, an aralkyl group, an acyloxyalkyl group or an epoxyalkyl group.

14. The synthetic polymer composition according to claim 13 wherein said compound (I) is incorporated in an amount of 0.01 – 5.0% by weight, based upon the amount of the synthetic polymer.

15. The synthetic polymer composition according to claim 13 wherein said polymer is a polyolefin.

16. The synthetic polymer composition according to claim 13 wherein said polymer is a polyvinyl chloride.

17. The synthetic polymer composition according to claim 13 wherein said polymer is a polyurethane.

18. The synthetic polymer composition according to claim 13 wherein said polymer is a polyamide.

19. The synthetic polymer composition according to claim 13 wherein said polymer is a polyacetal.

20. The synthetic polymer composition according to claim 13 wherein said polymer is a polyester.

21. The synthetic polymer composition according to claim 13 wherein said compound is selected from the group consisting of 1,3,8-triaza-3-butyl-7,7,8,9,9-pentamethyl-spiro[4.5]decane-2,4-dione,
1,3,8-triaza-7,7,8,9,9-pentamethyl-3-octyl-spiro[4.5]decane-2,4-dione,
8-allyl-1,3,8-triaza-7,7,9,9-tetramethyl-3-octyl-spiro[4.5]-decane-2,4-dione,
1,3,8-triaza-8-benzyl-7,7,9,9,-tetramethyl-3-octyl-spiro[4.5]decane-2,4-dione,
1,3,8-triaza-8-(2-hydroxyethyl)-7,7,9,9-tetramethyl-3-octyl-spiro[4.5]decane-2,4-dione,
1,3,8-triaza-3-butyl-8-(2,3-epoxypropyl)-7,7,9,9-tetramethyl-spiro[4.5]decane-2,4-dione,
3-allyl-1,3,8-triaza-7,7,8,9,9-pentamethyl-spiro[4.5]decane-2,4-dione,
3,8-diallyl-1,3,8-triaza-7,7,9,9-tetramethyl-spiro[4.5]decane-2,4-dione,
3-allyl-1,3,8-triaza-8-(2,3-epoxypropyl)-7,7,9,9-tetramethyl-spiro[4.5]decane-2,4-dione,
3,8-bis(2,acetoxyethyl)-1,3,8-triaza-7,7,9,9-tetramethyl-spiro[4.5]decane-2,4-dione,
1,3,8-triaza-3-(2,3-epoxypropyl)-7,7,8,9,9-pentamethyl-spiro[4.5]decane-2,4-dione,
1,3,8-triaza-3,8-bis(2,3-epoxypropyl)-7,7,9,9-tetramethylspiro[4.5]decane-2,4-dione,
1,3,8-triaza-3,8-dibenzyl-1,7,7,9,9-pentamethyl-spiro[4.5]decane-2,4-dione, and
1,3,8-triaza-1,3,7,7,8,9,9-heptamethyl-spiro[4.5]-decane-2,4-dione.

22. A synthetic polymer composition stabilized against photo- and thermal-deterioration wherein there is incorporated, in a sufficient amount to prevent said deterioration, a compound having the formula

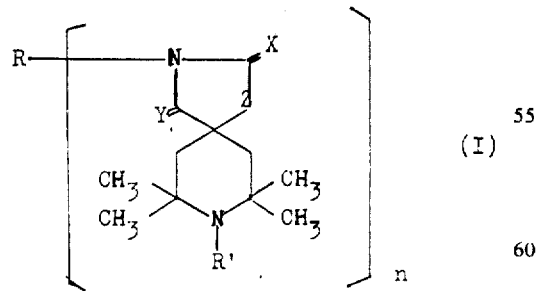

(I)

wherein
R' represents an alkyl group, a substituted alkyl group, an acyl group, an alkoxycarbonyl group, a substituted alkoxycarbonyl group, an amino group, a substituted amino group or
nitroso group;
X and Y represent oxygen;

Z represents a group of the formula >N-R''' in which R''' is hydrogen atom, an alkyl group or a substituted alkyl group;
n is an integer of 1 through 4 inclusive; and
R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group,
when n is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group,
when n is 3, an alkanetriyl group, a tris-(acyloxyalkylene) group, an alkane-tris-(oxycarbonylalkyl) group or a group of the group

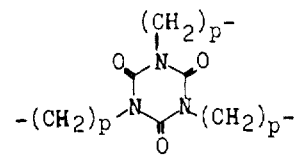

in which
p is an integer of 1 through 8 inclusive and p's may be the same or different, and,
when n is 4, an alkane tetrayl group, a tetrakis-(acyloxyalkylene) group or an alkanetetrakis(oxycarbonylalkyl) group.

23. The synthetic polymer composition according to claim 22 wherein said compound (I) is a member selected from the compounds (I) in which
R' represent an alkyl group of 1 to 20 carbon atoms, a hydroxyalkyl group, an allyl group, 2-propynyl group, a cyanoalkyl group, an alkoxyalkyl group, an alkenyloxyalkyl group, an aryloxyalkyl group, an alkylthioalkyl group, an epoxyalkyl group, an acyloxyalkyl group, an alkoxycarbonylalkyl group, an aralkyl group, an acryloyl group, an acryloyl group which is substituted with alkyl or phenyl, an aralkyloxycarbonyl group, an amino group or an amino group which is substituted with aroyl or alkyl;
R represents, when n is 1, the above-defined alkyl group, a phenyl or naphtyl group which may be substituted with halogen or alkyl in the aryl moiety, a cycloalkyl group, an alkoxycarbonyl group, an aralkyloxycarbonyl group, the group of the formula

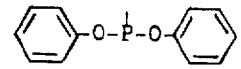

or the group of the formula

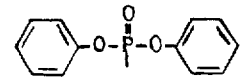

when n is 2, a polymethylene group of 1 to 10 carbon atoms, a group of the formula —(CH$_2$)$_p$—CH=CH—(CH$_2$)$_p$— in which p is an integer of 1 through 8 inclusive and p's may be the same or different, a phenylene group which may be substituted with alkyl, a group of the formula $$-CH_2-\text{[phenylene]}-CH_2-$$

a group of the formula $$-\text{[phenyl]}-CH_2-\text{[phenyl]}-$$

a group of the formula $$-(CH_2)_p-\overset{O}{\overset{\|}{C}}-(CH_2)_{p_1}-\overset{O}{\overset{\|}{C}}-(CH_2)_p-$$

in which $p$ is as defined above and $p_1$ is an integer of zero through 8 inclusive, a group of the formula $$-(CH_2)_p-\overset{O}{\overset{\|}{OC}}-\text{[phenylene]}-\overset{O}{\overset{\|}{CO}}-(CH_2)_p-$$

in which $p$ is as defined above, a group of the formula $$-(CH_2)_p-\overset{O}{\overset{\|}{CO}}-(CH_2)_p-\overset{O}{\overset{\|}{OC}}-(CH_2)_p-$$

in which $p$ is as defined above, a group of the formula $-(CH_2)_p-O-(CH_2)_p-$ in which $p$ is as defined above or a group of the formula $$-\text{[phenyl]}-O-\text{[phenyl]}-$$

when $n$ is 3, a group of the formula $$-(CH_2)_p-CH\begin{matrix}(CH_2)_p-\\(CH_2)_p-\end{matrix}$$

in which $p$ is as defined above, a group of the formula $$\begin{matrix}CH_2-COO(CH_2)_p-\\CH-COO(CH_2)_p-\\CH_2-COO(CH_2)_p-\end{matrix}$$

in which $p$ is as defined above, a group of the formula $$\text{[phenyl]}\begin{matrix}-COO(CH_2)_p-\\-COO(CH_2)_p-\\-COO(CH_2)_p-\end{matrix}$$

in which $p$ is as defined above, a group of the formula $$\begin{matrix}CH_2-OCO(CH_2)_p-\\CH-OCO(CH_2)_p-\\CH_2-OCO(CH_2)_p-\end{matrix}$$

in which $p$ is as defined above or a group of the formula $$-(CH_2)_p-N\begin{matrix}O\\\|\\C\end{matrix}\begin{matrix}(CH_2)_p-\\N\\\end{matrix}\begin{matrix}O\\\|\\C\end{matrix}N-(CH_2)_p-$$

in which $p$ is as defined above, and, when $n$ is 4, a group of the formula $$\begin{matrix}-(CH_2)_p\\-(CH_2)_p\end{matrix}C\begin{matrix}(CH_2)_p-\\(CH_2)_p-\end{matrix}$$

in which $p$ is as defined above, a group of the formula $$\text{[phenyl]}\begin{matrix}-COO(CH_2)_p-\\-COO(CH_2)_p-\\-COO(CH_2)_p-\\-COO(CH_2)_p-\end{matrix}$$

in which $p$ is as defined above or a group of the formula $$\begin{matrix}-(CH_2)_p-COOCH_2\\-(CH_2)_p-COOCH_2\end{matrix}C\begin{matrix}CH_2OCO(CH_2)_p-\\CH_2OCO(CH_2)_p-\end{matrix}$$

in which $p$ is as defined above, $p$'s being optionally the same or different.

24. A synthetic polymer composition stabilized against photo- and thermal-deterioration wherein there is incorporated, in a sufficient amount to prevent said deterioration, a compound having the formula $$R-\left[\begin{matrix}N\overset{X}{\diagup}\\\quad\quad Z\\Y\\H_3C\quad CH_3\\H_3C\overset{\text{[piperidine]}}{\underset{R'}{N}}CH_3\end{matrix}\right]_n$$

wherein
R' represents an alkyl group, an alkenyl group, an aralkyl group, an acyloxyalkyl group, a hydroxyalkyl group or an epoxyalkyl group;
X and Y represent oxygen;

Z represents a group of the formula >N—R''' in which R''' is hydrogen atom or an alkyl group;
n is 2, and
R represents an alkylene group, a group of the formula
or a group of the formula —(CH$_2$)$_p$—O—(CH$_2$)$_p$— in which p is an integer of 1 through 8 inclusive.
* * * * *